(12) United States Patent
Berto et al.

(10) Patent No.: US 9,494,522 B2
(45) Date of Patent: Nov. 15, 2016

(54) DEVICE AND METHOD FOR STIMULATED RAMAN DETECTION

(71) Applicants: UNIVERSITÉ AIX-MARSEILLE, Marseilles (FR); CENTRE NATIONAL DE LA RECHERCHE SCIENTIFIQUE, Paris (FR)

(72) Inventors: Pascal Berto, Marseilles (FR); Esben Andresen, Marseilles (FR); Hervé Rigneault, Allauch (FR)

(73) Assignees: Université Aix-Marseille, Marseilles (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 14/780,003

(22) PCT Filed: Mar. 25, 2014

(86) PCT No.: PCT/EP2014/055987
§ 371 (c)(1),
(2) Date: Sep. 25, 2015

(87) PCT Pub. No.: WO2014/154708
PCT Pub. Date: Oct. 2, 2014

(65) Prior Publication Data
US 2016/0047750 A1 Feb. 18, 2016

(30) Foreign Application Priority Data
Mar. 26, 2013 (FR) .................................. 13 00694

(51) Int. Cl.
*G01J 3/44* (2006.01)
*G01N 21/65* (2006.01)

(52) U.S. Cl.
CPC ......... *G01N 21/65* (2013.01); *G01N 2021/655* (2013.01); *G01N 2201/06113* (2013.01)

(58) Field of Classification Search
CPC ................................. G01N 21/65; G01J 3/44
See application file for complete search history.

(56) References Cited

U.S. PATENT DOCUMENTS

| 6,798,507 B2 * | 9/2004 | Xie ........................... G01J 3/44 356/301 |
| 6,809,814 B2 * | 10/2004 | Xie ........................... G01J 3/44 356/301 |

(Continued)

FOREIGN PATENT DOCUMENTS

EP 2211219 A2 7/2010

OTHER PUBLICATIONS

International Search Report issued in PCT/EP2014/055987 mailed on May 27, 2014 (3 pages).

(Continued)

*Primary Examiner* — Tarifur Chowdhury
*Assistant Examiner* — Jamil Ahmed
(74) *Attorney, Agent, or Firm* — Osha Liang LLP

(57) ABSTRACT

According to one aspect, the invention relates to a device for detecting a resonant non-linear optical signal of Stimulated Raman Scattering (SRS) type induced in a sample. The device comprises electro-optical means for making interact in the sample, at a first modulation frequency, trains of light pulses of angular frequencies $\omega_1$ and $\omega_2$ and, at a second modulation frequency, trains of light pulses of angular frequencies $\omega_2$ and $\omega_3$, such that $\omega_2-\omega_1=\omega_3-\omega_2=\Omega_R$ where $\Omega_R$ is a molecular vibrational resonant angular frequency of the sample. Moreover, the device comprises means for synchronous detection at the first and second modulation frequencies of non-linear optical signals resulting from the interaction of the light pulses in the sample, and electronic processing means making it possible to obtain, from electronic signals resulting from the synchronous detection, a signal characterizing the molecular vibrational resonance of the sample.

20 Claims, 26 Drawing Sheets

(56) References Cited

U.S. PATENT DOCUMENTS

| | | | | |
|---|---|---|---|---|
| 7,352,458 | B2* | 4/2008 | Xie | G01J 3/433 356/301 |
| 7,616,304 | B2* | 11/2009 | Gankkhanov | G01J 3/10 356/301 |

OTHER PUBLICATIONS

Written Opinion of the International Searching Authority issued in PCT/EP2014/055987 mailed on May 27, 2014 (7pages).

Freudiger, C.W. et al.; "Highly specific label-free molecular imaging with spectrally tailored excitation-stimulated Raman scattering (STE-SRS) microscopy"; Nature Photonics, XP055091658, vol. 5, No. 2, Jan. 16, 2011, pp. 103-109 (7 pages).

Popov, K.I.. et al.; "Image formation in CARS and SRS: effect of an inhomogeneous nonresonant background medium"; Optics Letters, XP-001574102, vol. 37, No. 4, Feb. 15, 2012, pp. 473-475 (3 pages).

Jin, S.M. et al.; "Development of Femtosecond Stimulated Raman Spectroscopy: Stimulated Raman Gain via Elimination of Cross Phase Modulation"; Bulletin of the Korean Chemical Society, XP008142647, vol. 25, No. 12, Dec. 20, 2004, pp. 1829-1832 (4 pages).

N. Bloembergen; "The Stimulated Raman Effect"; American Journal of Physics, vol. 35, No. 11, pp. 989-1023; Nov. 1967 (35 pages).

N. Huang et al.; "Full range characterization of the Raman spectra of organs in a murine model"; Optics Express, vol. 19, No. 23, pp. 22892-22909; Oct. 27, 2011 (18 pages).

Y. Ozeki et al.; "Analysis and experimental assessment of the sensitivity of stimulated Raman scattering microscopy"; Optics Express, vol. 17, No. 5, pp. 3651-3658; Feb. 24, 2009 (8 pages).

P. Nandakumar et al.; "Vibrational imaging based on stimulated Raman scattering microscopy"; New Journal of Physics, 11, pp. 1-9; Mar. 25, 2009 (9 pages).

C. W. Freudiger, et al.; "Label-Free Biomedical Imaging with High Sensitivity by Stimulated Raman Scattering Microscopy"; Science, vol. 322, pp. 1857-1861; Dec. 19, 2008 (6 pages).

* cited by examiner

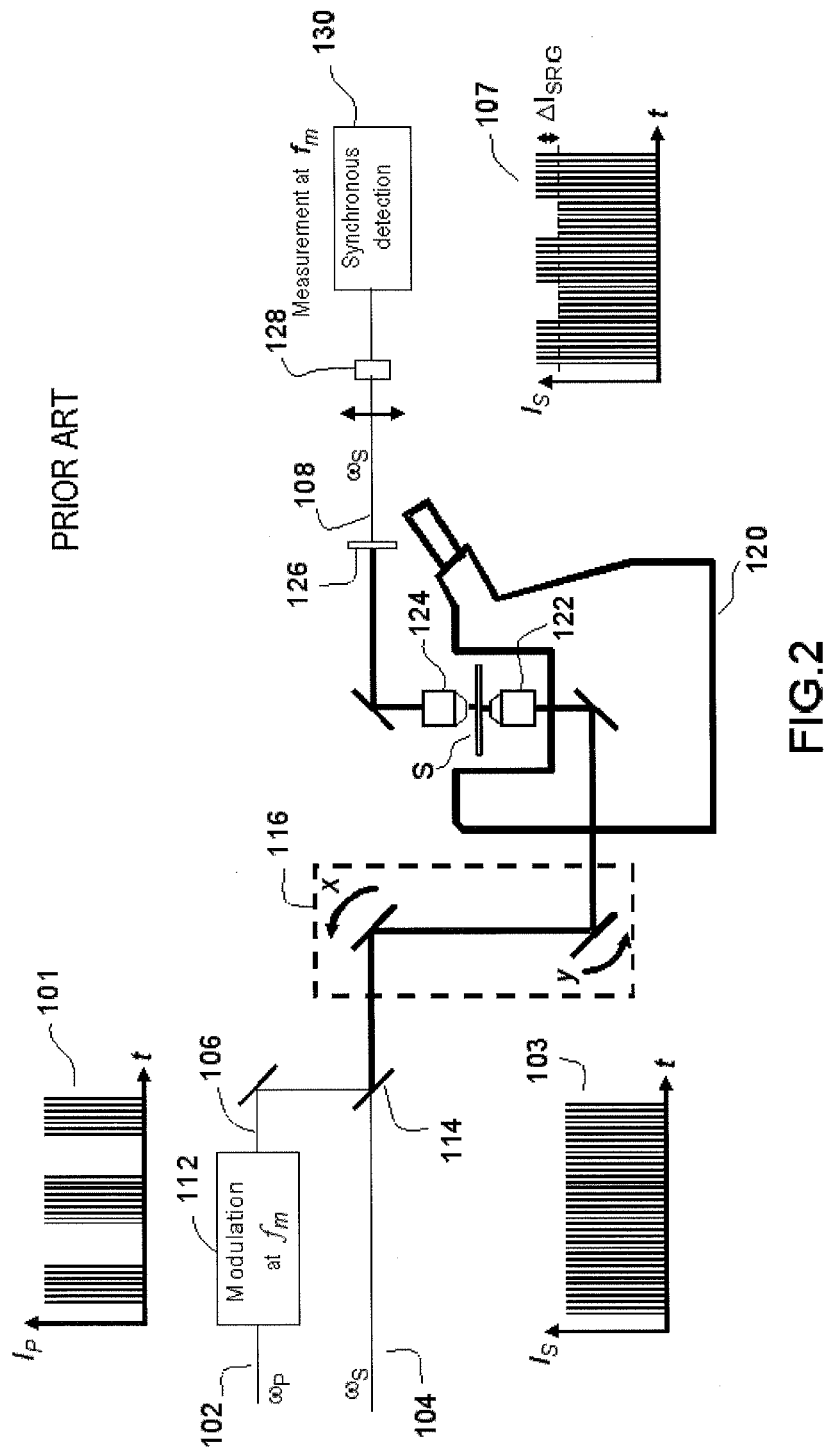

PRIOR ART

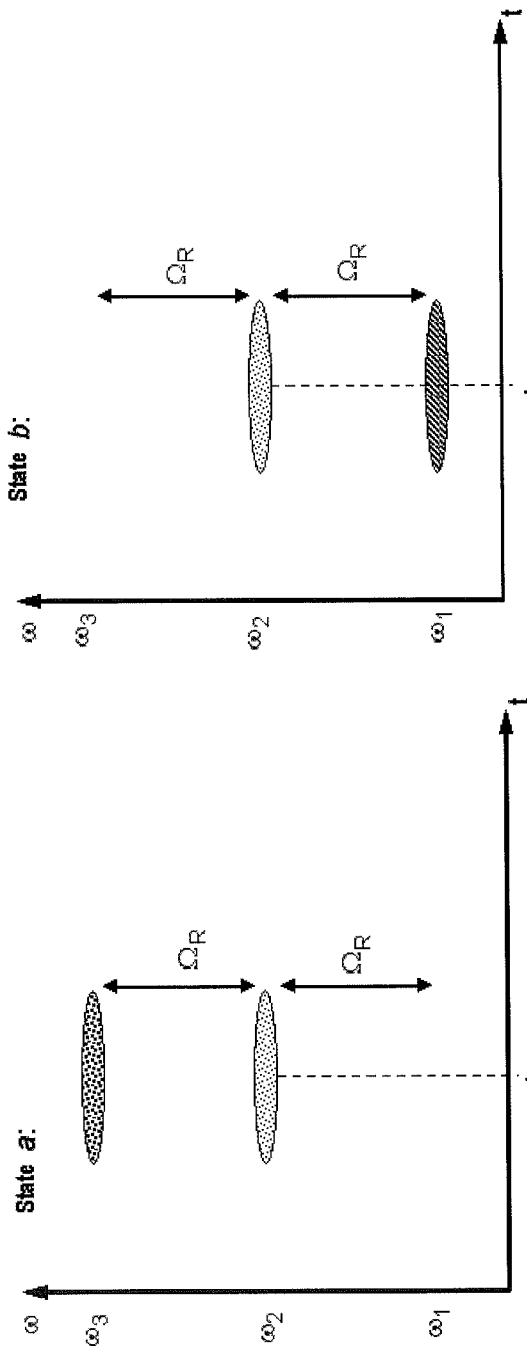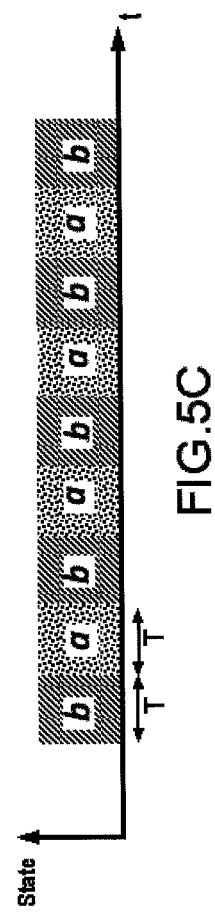

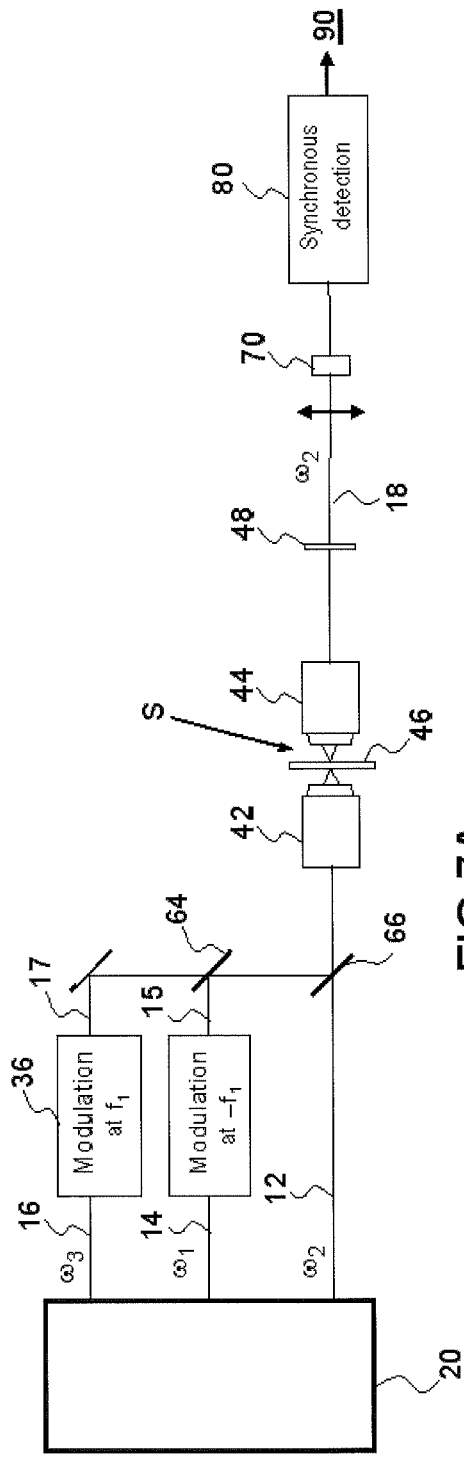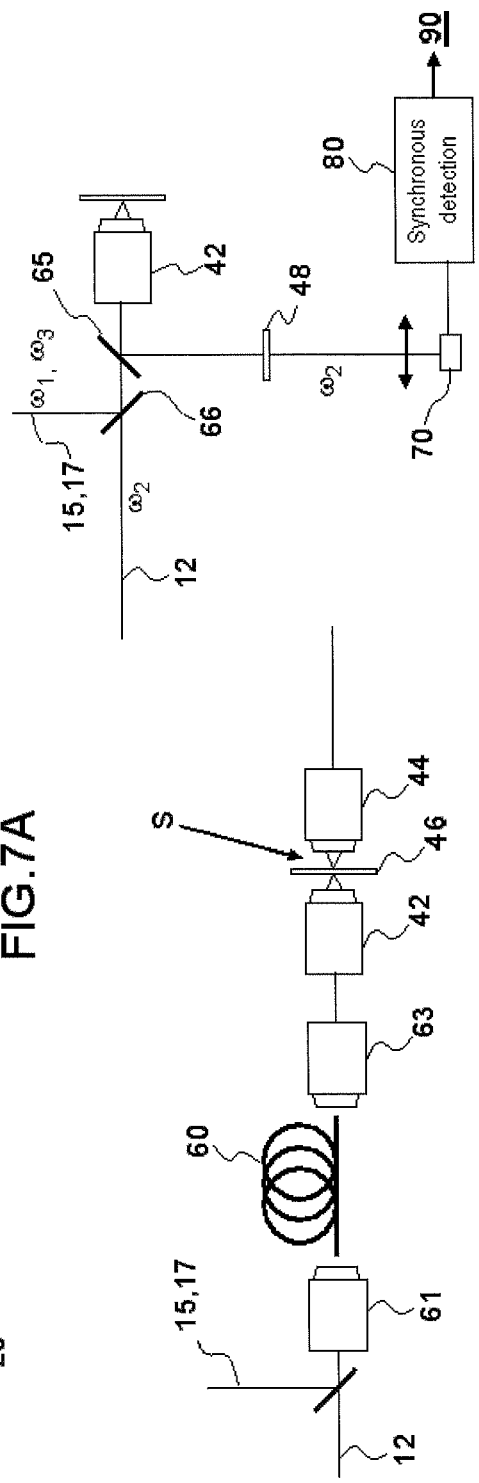
FIG.7A
FIG.7B
FIG.7C

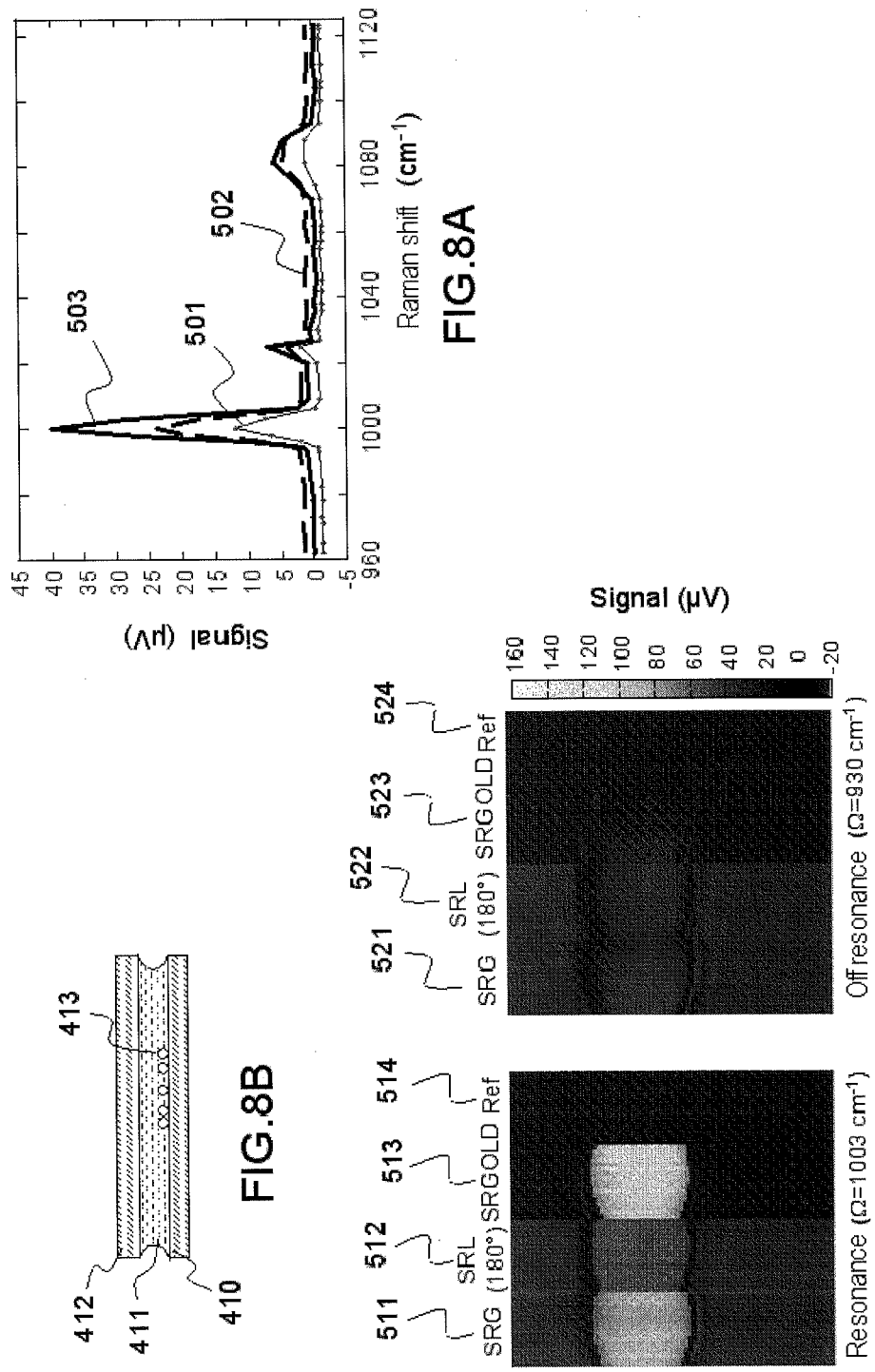

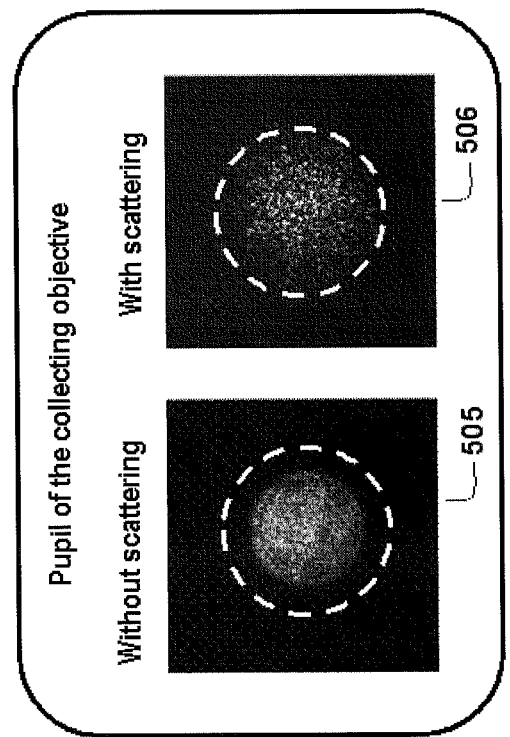
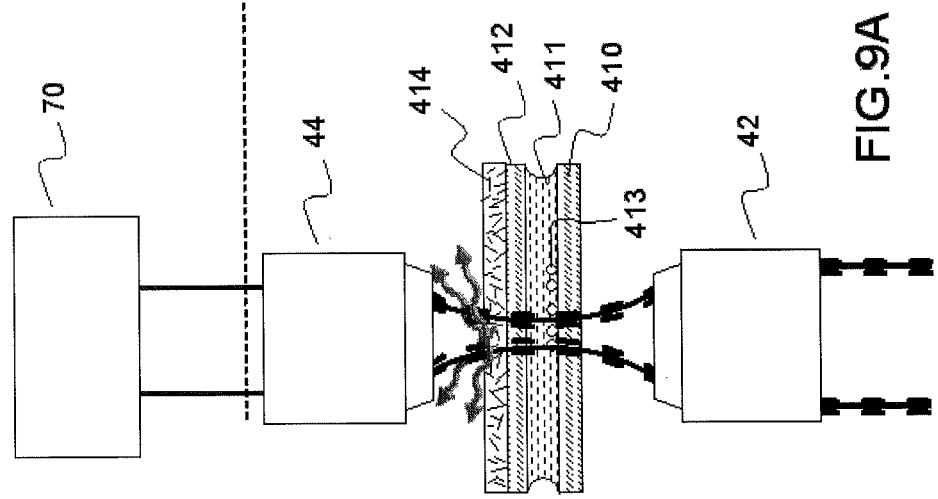
FIG. 9B
FIG. 9A

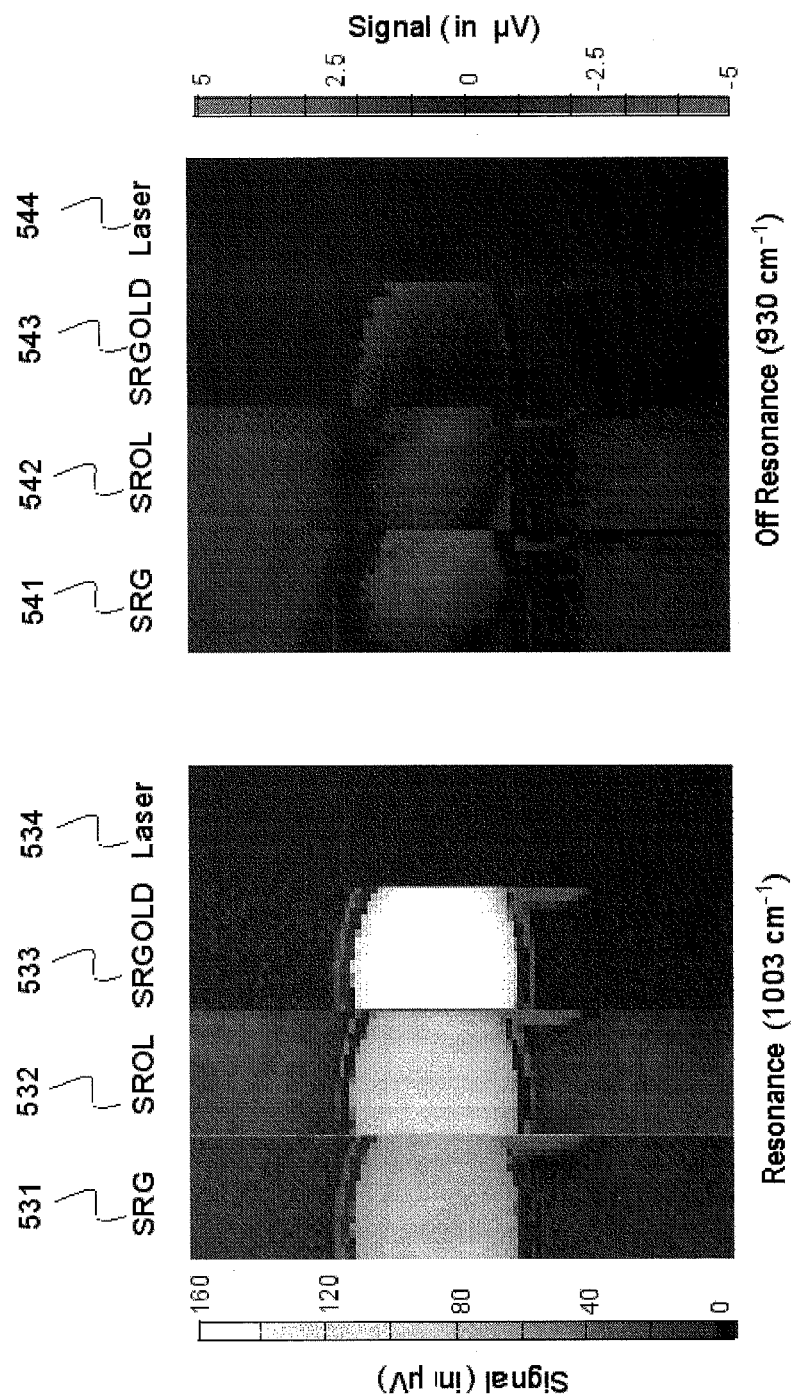

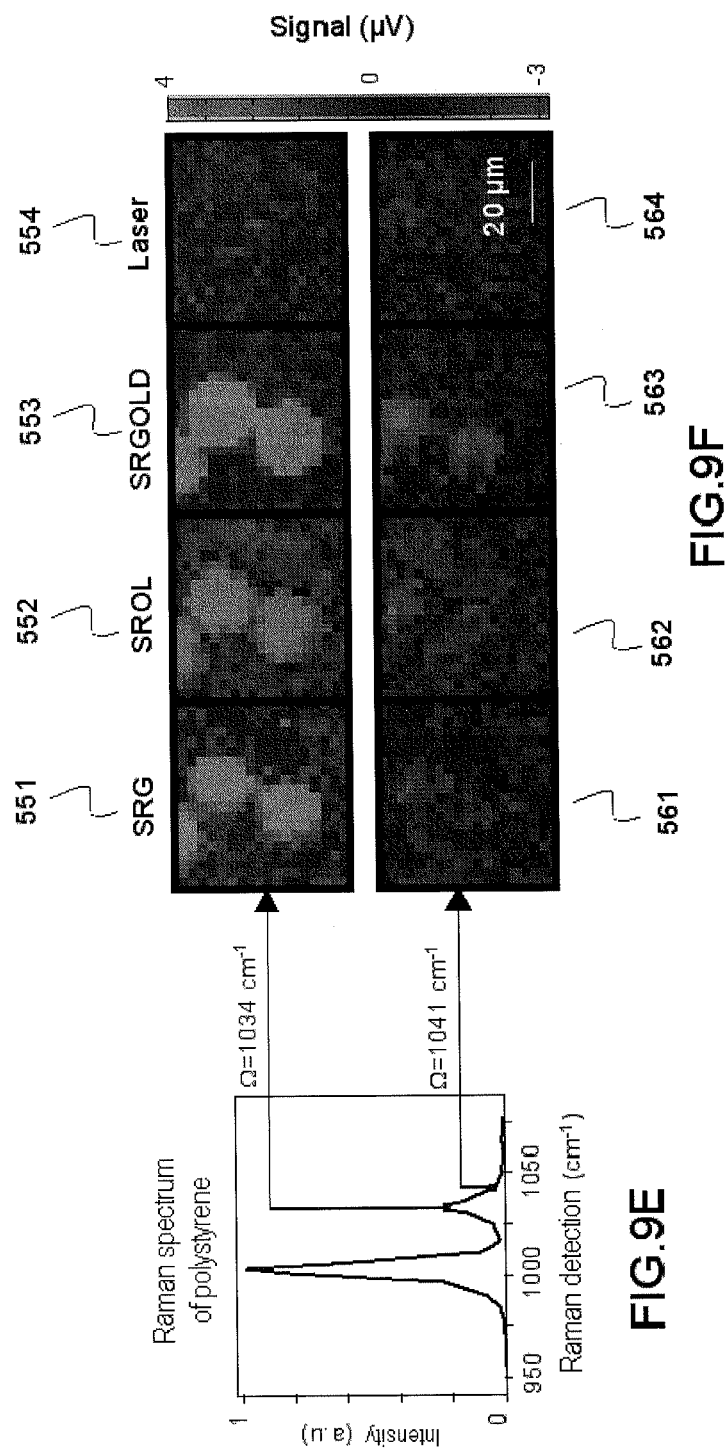

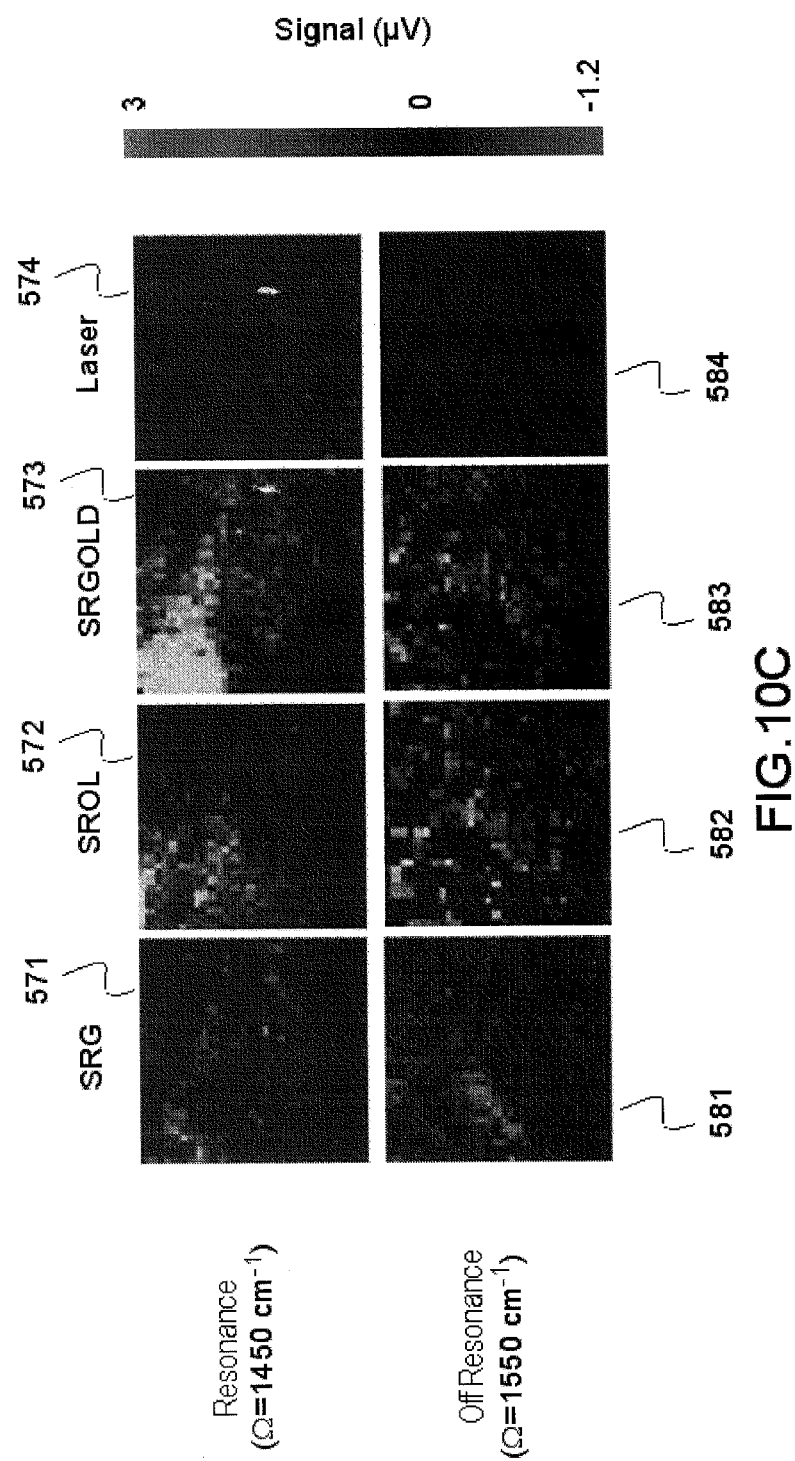

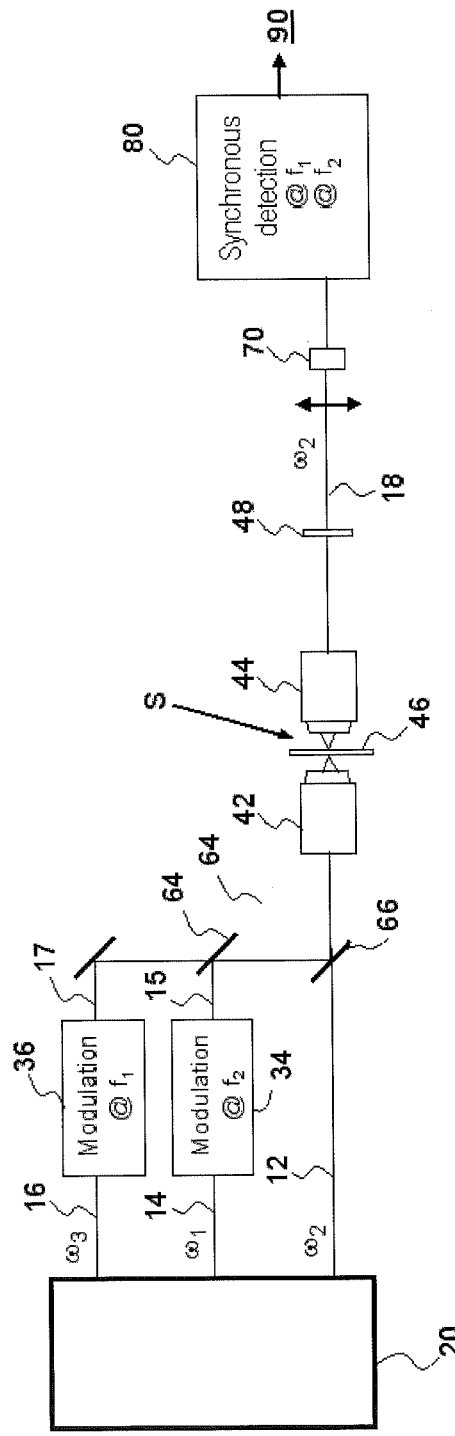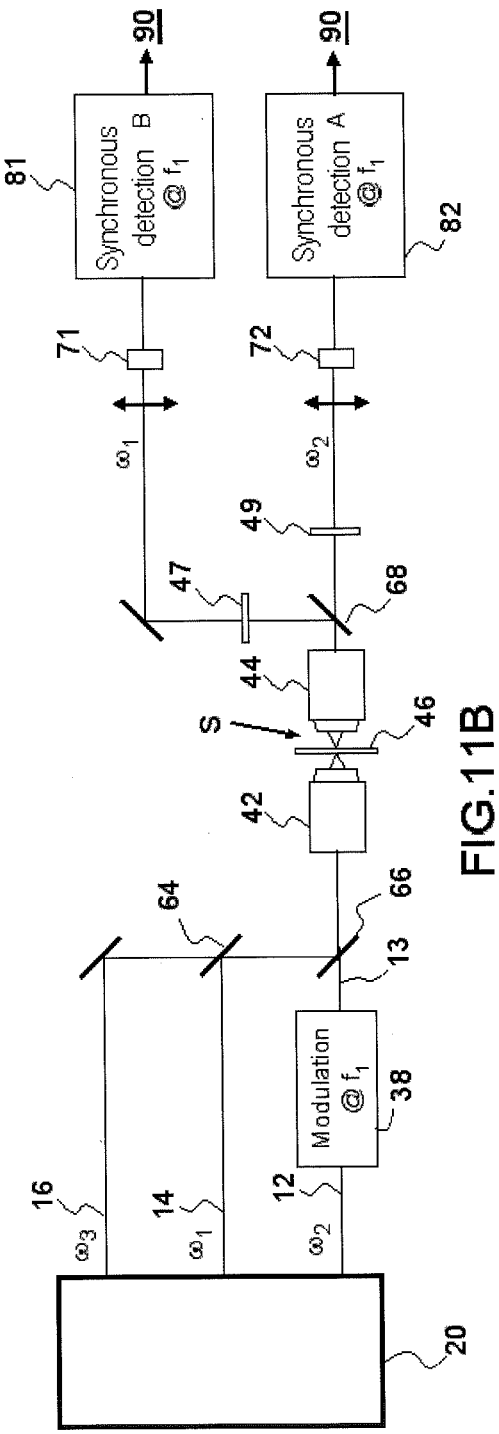
FIG.11A
FIG.11B

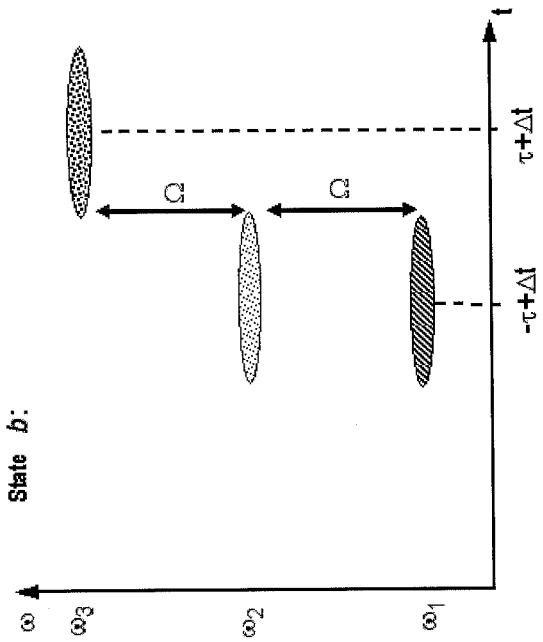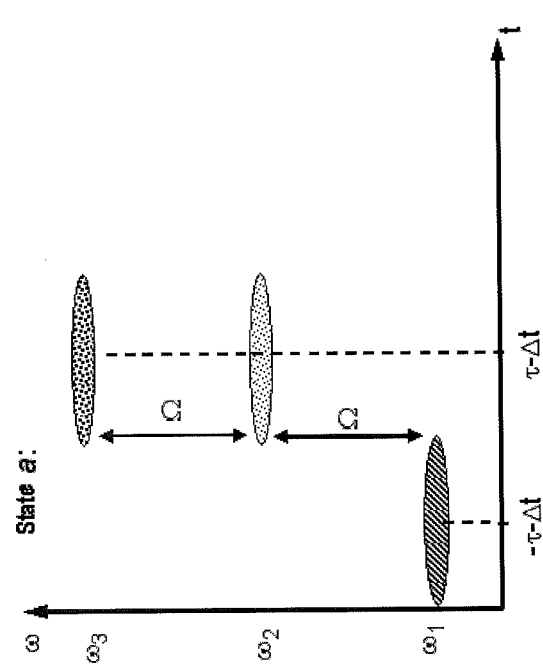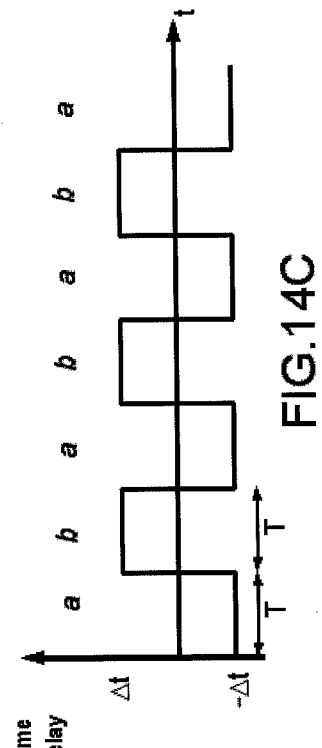
FIG.14A
FIG.14B
FIG.14C

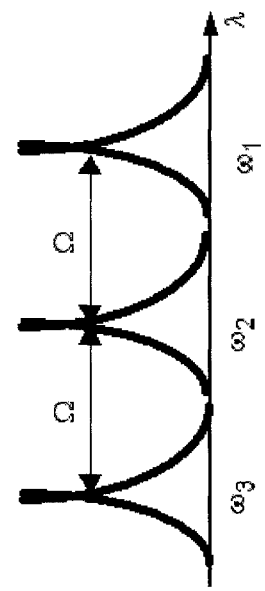
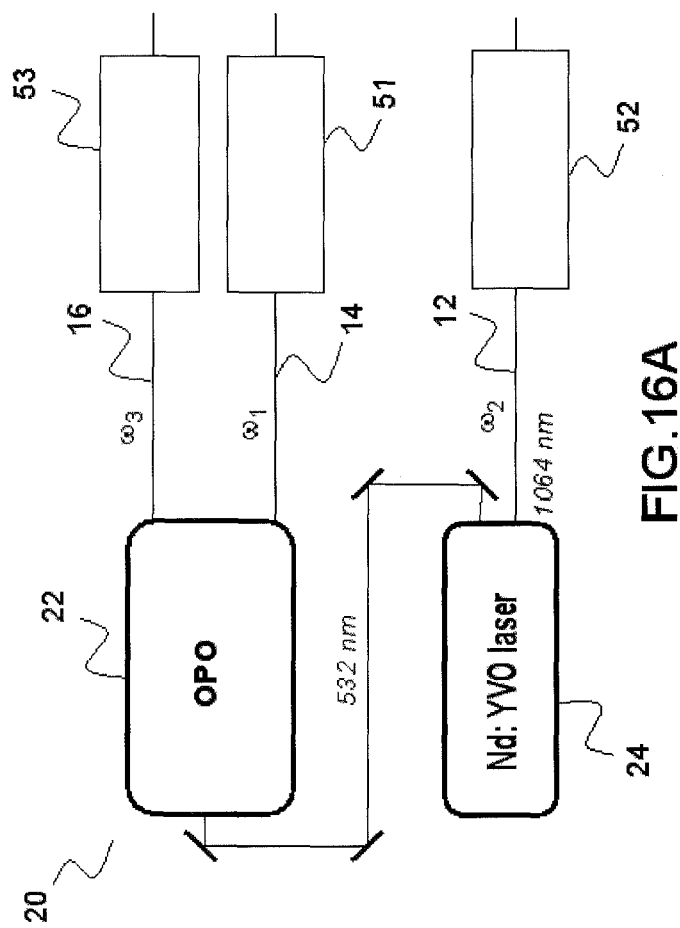
FIG.16A
FIG.16B

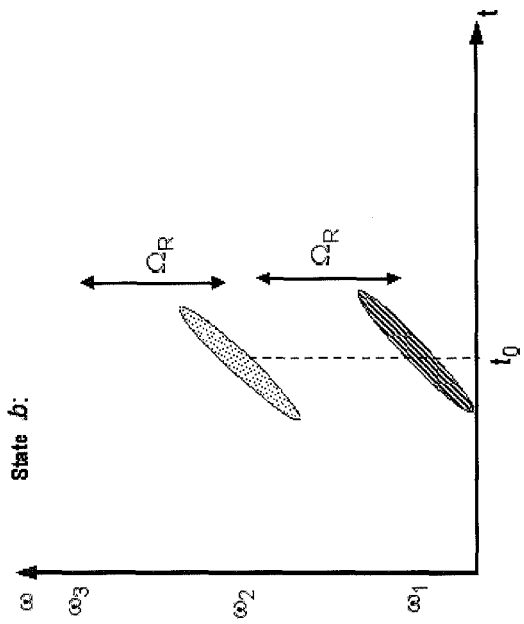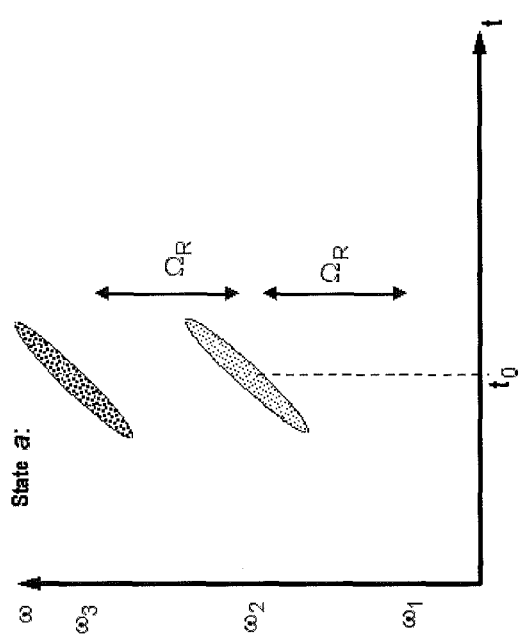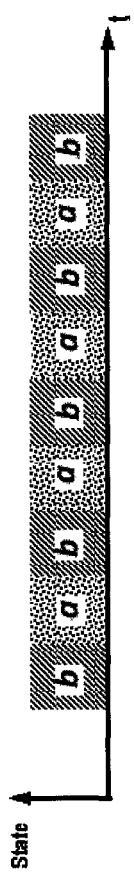
FIG. 17A
FIG. 17B
FIG. 17C

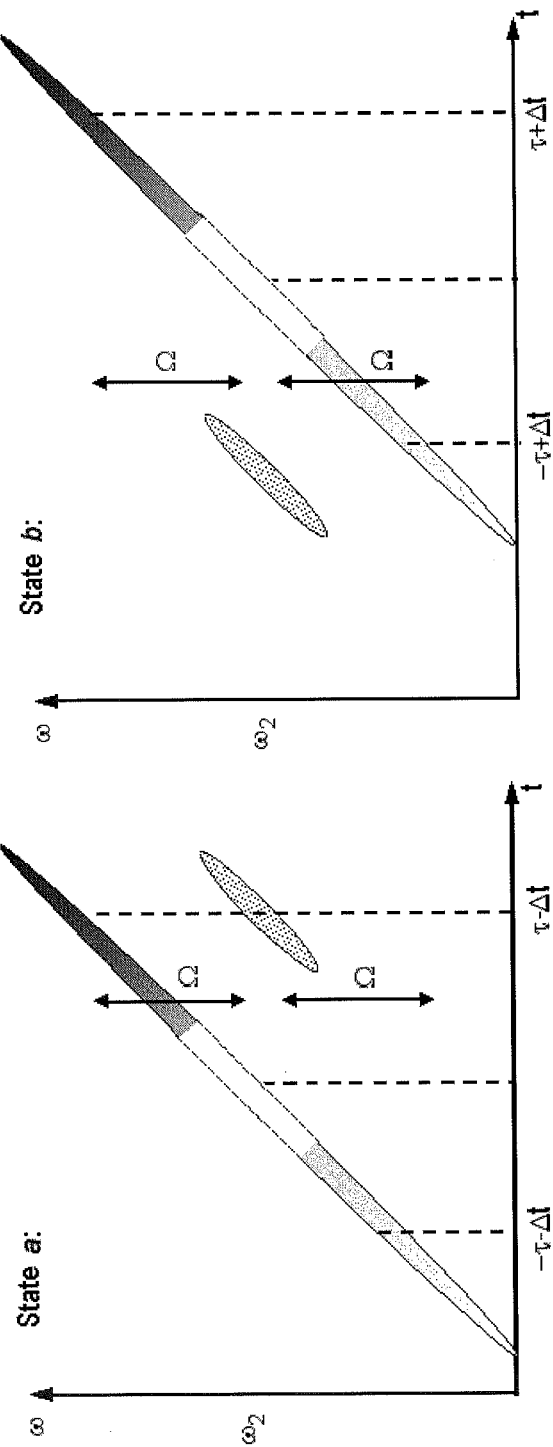
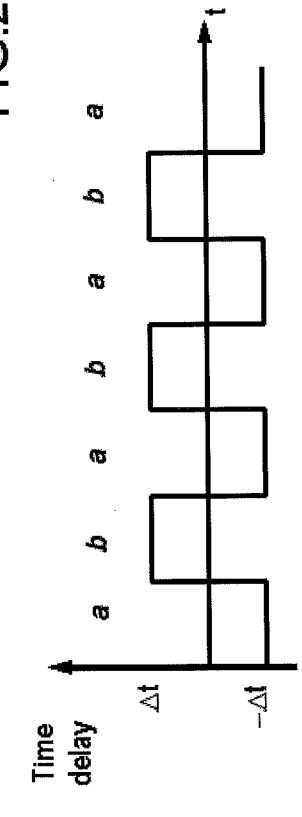
FIG.21A
FIG.21B
FIG.21C

DEVICE AND METHOD FOR STIMULATED RAMAN DETECTION

TECHNICAL FIELD OF THE INVENTION

The present invention relates to a device and a method for detection of a resonant non-linear optical signal of Stimulated Raman Scattering (SRS) type in a sample. It is especially applicable to microscopy imaging, to spectroscopy and to hyperspectral imaging in scattering media such as biological media.

PRIOR ART

Every chemical bond possesses vibrational frequencies that are specific to it. Methods that aim to use interaction between light and matter to obtain information on these molecular vibrations are called vibrational optical techniques. The best-known of these techniques is infrared (IR) spectroscopy, in which specific absorption lines of chemical bonds present in a sample are observed. Discovered in 1928, Raman scattering (named after the physicist Chandrasekhara Venkata Raman who discovered the effect) allows visible light to be used to obtain the vibrational spectrum of molecules that interact with light beams. In a Raman scattering process, a pump wave of angular frequency $\omega_P$ incident on a molecule is inelastically scattered into what is called a Stokes wave of angular frequency $\omega_S$ and what is called an anti-Stokes wave of angular frequency $\omega_{AS}$. The frequency difference between the generated waves and the pump wave depends on the molecular Raman transition (of angular frequency $\Omega_R$) such that $\omega_P - \omega_S = \omega_{AS} - \omega_P = \Omega_R$. From a photonic point of view of the process, the Stokes and anti-Stokes waves correspond to absorption from the fundamental or excited vibrational level, respectively. The process generating the anti-Stokes wave, from the excited vibrational level, is much less probable than the process creating the Stokes wave, which is the only wave observed in practice in spontaneous Raman spectroscopy. A close study of the spectral distribution of the Stokes waves provides information on the density of chemical bonds present in the sample. This spontaneous inelastic scattering process is very ineffective in comparison to fluorescence (Raman effective cross-sections are of the order of $10^{-30}$ cm$^2$/molecule, to be compared with the 1-photon effective absorption cross-section of a fluorophore, which reaches $10^{-16}$ cm$^2$/molecule).

The stimulated Raman techniques called Coherent Anti-Stokes Raman Scattering (CARS) and Stimulated Raman Scattering (SRS) are coherent Raman scattering processes that, relative to spontaneous Raman scattering processes, provide an amplification of about $10^7$. In these techniques (see FIG. 1A) two laser pulses of angular frequency $\omega_p$ and $\omega_s$ (or of frequencies $\nu_p$ and $\nu_s$), the angular frequency difference of which is set equal to the angular frequency $\Omega_R$ of the vibrational level that it is desired to probe, are injected into the medium to be analyzed. These pulses, denoted the pump and Stoke pulses, respectively, create frequency beating that causes the vibrational mode of angular frequency $\Omega_R$ to enter into resonance. In the CARS process, this resonance is probed by the pump beam, which induces anti-Stokes scattering at the angular frequency $\omega_{AS}$. Stimulated Raman Scattering (SRS) is a process that makes use of the non-linear response due to the interaction of the non-linear field induced by the pump and Stokes fields with the exciting (pump) field, and it is therefore, in contrast to the CARS process, observed at the same frequencies as the pump and Stokes pulses. It leads to a transfer of energy from the pump beam to the Stokes beam. Thus, Stimulated Raman Scattering covers two processes, the SRL (for stimulated Raman loss) process and the SRG (for stimulated Raman gain) process, which induce an intensity loss $\Delta I_{SRL}$ in the pump beam and an intensity gain $\Delta I_{SRG}$ in the Stokes beam, respectively (see FIG. 1B). The SRS process is for example described in the review article by N. Bloembergen ("The stimulated Raman effect", American Journal of Physics, 35:989-1023, 1967). It has been shown that the decrease $\Delta I_{SRL}$ in the intensity of the pump beam and the gain $\Delta I_{SRG}$ in the intensity of the Stokes beam are proportional to the imaginary part of the 3rd order non-linear susceptibility ($\text{Im}(\chi_R^{(3)})$). Measurement of these quantities therefore makes a rigorous calculation of the Raman spectrum possible. Recently, vibrational optical techniques have concentrated more on SRS techniques, which, in contrast to CARS techniques, are not subject to a non-resonant background, which is always present in CARS, and which are linear with chemical species concentration.

SRS microscopy is a new technique that takes advantage of recent advances in the field of femtosecond SRS spectroscopy. In 2007, Ploetz et al. ("Femtosecond Stimulated Raman Microscopy", Applied Physics B, 87(3):389-393, 2007) developed the first SRS microscope based on an amplified laser system delivering femtosecond and picosecond pulses. This type of system induces a strong SRS signal but is not however suitable for biological imaging. Specifically, the high peak powers employed (of the order of a nJ) damage the samples, and the low repetition rates (1 kHz) are incompatible with fast-scanning microscopy.

An SRS microscope based on the use of a high repetition rate (80 MHz) picosecond laser system, compatible with the formation of images of biological samples, was then proposed (see for example the articles by C. W. Freudiger et al.: "Label-free biomedical imaging with high sensitivity by stimulated Raman scattering microscopy", Science, 322 (5909):1857-1861, 2008, P. Nandakumar et al.: "Vibrational imaging based on stimulated Raman scattering microscopy", New Journal of Physics, 11(3):033026 (9 pp), 2009, Y. Ozeki et al.: "Analysis and experimental assessment of the sensitivity of stimulated Raman scattering microscopy", Optics Express, 17(5):3651-3658, March 2009). In CARS microscopy, the useful signal, i.e. the anti-Stokes signal, is generated at a different frequency from the exciting beams. The anti-Stokes signal may be detected by extremely sensitive detectors such as avalanche photodiodes or photomultiplier tubes. In SRS microscopy, detection poses a different problem because the useful signal is generated at the same frequency as the exciting beams. It is thus a question of either detecting the energy $\Delta I_{SRL}$ loss from the pump beam, or of detecting the energy $\Delta I_{SRG}$ gain in the Stokes beam. In practice, the energy loss from the pump beam is of the order of $\Delta I_{SRL}/I_P \approx 10^{-5} - 10^{-8}$. In the articles cited above, it is suggested to modulate the Stokes signal at a frequency $f_m$ and to extract the loss from the pump signal at the frequency $f_m$ by synchronous detection in order to increase detection sensitivity.

Thus, FIG. 2 shows a schematic of a prior-art SRS microscope in SRG configuration, i.e. in a configuration adapted to extract the gain from the Stokes beam. Trains of pump and Stokes pulses, referenced 102 and 104 in FIG. 2, at angular frequencies $\omega_p$ and $\omega_S$ respectively, are injected into a sample S positioned at the focal point of a microscope objective 122 arranged in the body of a microscope 120. The angular frequencies $\omega_p$ and $\omega_S$ are chosen in such a way that the angular frequency difference is equal to an angular frequency $\Omega_R$ of the vibrational level that it is desired to probe in the sample. The pump and Stokes pulse trains are spatially superposed by means of a combiner 114, and a variable delay line (not shown) is provided to ensure the temporal superposition of the pulses in the sample. The pump pulse train 102 is amplitude modulated at the modulation frequency $f_m$ by means of a modulating device 112 in order to form a modulated pulse train 106. In order to decrease the electronic noise and the noise of the laser, the modulation frequency is chosen to be above 1 MHz. Thus, in FIG. 2 the curves 101 and 103 show the time waveform of the light intensities $I_P$ and $I_S$ of the modulated pump pulse train 106 and the (unmodulated) Stokes pulse train 104, respectively. A collecting objective 124 allows the optical signals resulting from the interaction of the pump and Stokes pulses in the sample to be collected. In the chosen configuration, a filter 126 allows the train 108 of pulses at the angular frequency $\omega_S$ to be selected, which train is then transmitted to an optical detector 128, for example a photodiode. The optical intensity measured as a function of time is schematically shown by the curve 107. Synchronous detection 130 at the modulation frequency $f_m$ allows the sought-after signal $\Delta I_{SRG}$ characterizing the molecular vibration at the angular frequency $\Omega_R$ to be extracted. Scanning the exciting beams 104, 106 over the sample, for example by means of a scanning system 116 comprising two galvanometer mirrors, then allows an image of the zone of interest of the sample to be formed.

However, SRS microscopy is subject to a number of artifacts that limit chemical specificity because they introduce signals that can be interpreted as the SRS signal. In particular, SRS microscopy is sensitive to the cross Kerr effect (or XPM for "cross phase modulation"), which is not specific to the targeted chemical bonds and which appears as a positive or negative offset in the SRS signal. SRS microscopy is also sensitive to two-photon absorption (or TPA for "two-photon absorption"), which appears as a positive (in SRL configuration) or negative (in SRG configuration) offset in the SRS signal.

Two-photon absorption is an instantaneous non-linear process that (in the SRG configuration, such as shown in FIG. 2) induces a depletion of the Stokes beam only when the pump beam is present. The modulations induced in the Stokes beam are thus detected and interpreted as the SRS signal. In the SRG detection mode, depletion of the Stokes beam by TPA appears as a negative offset with respect to the SRG gain measurement. In the SRL detection mode, the depletion of the pump beam by TPA appears as a positive offset with respect to the SRL loss measurement.

The optical Kerr effect is a non-linear (instantaneous) process that induces a refractive index variation proportional to the intensity of the wave that generates it, and causes a lens effect that leads the beam generating it to focus or defocus. In SRS microscopy, the Kerr effect is not a problem when it affects only pump photons or only Stokes photons. Specifically, for example in the SRG configuration (such as shown in FIG. 2), when only pump photons are affected the Kerr effect induces a variation that is seen only by the pump beam; however, the latter is not detected, therefore its focus does not affect the measurement. When only Stokes photons are affected, the Kerr effect induces a variation that is seen only by the Stokes beam; since the latter is not modulated, its focus and the energy variation induced at the detector remain constant over time and therefore do not affect the SRS measurement at the modulation frequency $f_m$. However, for example in SRG configuration, a variation is observed in the refractive index at the angular frequency $\omega_s$ of the Stokes beam, which variation is induced by the pump beam of angular frequency $\omega_p$; this is the cross Kerr effect, which, in this case, focuses or defocuses the Stokes beam with the same modulation as that of the measured SRS signal. A measurement offset results. In order to reduce the influence of the cross Kerr effect, it is important not to introduce a diaphragm when collecting the measurement beam (pump in SRL, Stokes in SRG) after its interaction with the sample. For this reason, it is known to use a collecting objective the numerical aperture of which is larger than that of the excitation objective.

These artifacts are exacerbated by scattering media, especially biological tissues, and hinder the use of SRS microscopy to examine vibrational bonds having small effective Raman cross-sections. Specifically, even when a collecting objective having a numerical aperture larger than that of the excitation objective is used, scattering will lead to diaphragming by the collecting objective which exacerbates the effect of the artifacts, especially the cross Kerr effect.

Thus, FIGS. 3B to 3D illustrate spectra obtained by CARS, SRS and Raman micro-spectroscopy in various spectral regions, in a tissue formed from human skin, the Raman spectrum of which is shown in FIG. 3A. The spectrum shown in FIG. 3A, reproduced from the article by Huang et al. (Optics Express, 19, 23 (2011)) comprises three spectral regions of interest for Raman imaging. A region called the "lipids and proteins" region corresponding to angular frequencies between 2750 $cm^{-1}$ and 3050 $cm^{-1}$ and containing high-intensity molecular vibrations, a region called the "amides" region corresponding to angular frequencies between 1350 $cm^{-1}$ and 1750 $cm^{-1}$, and a region called the "fingerprints" region corresponding to angular frequencies between 850 $cm^{-1}$ and 1150 $cm^{-1}$. FIGS. 3B to 3D show spectral measurements carried out by CARS, SRS and Raman micro-spectroscopy, respectively, in each of these regions. In the regions where the intensity of the molecular vibrations is high (FIG. 3B), the SRS measurement 203 is seen to correspond well to the Raman spectrum 201, whereas the CARS measurement 202 exhibits an offset related to the continuous non-resonant background. The continuous non-resonant background effect in the CARS measurement is also visible in the two other regions (curves 212 and 222 in FIGS. 3C and 3D). Moreover, an offset (continuous background) is also observed to appear in the SRS measurement in the regions where the intensity of the molecular vibrations is lower. Thus, the curves resulting from the SRS measurements (213 and 223 in FIGS. 3C and 3D) no longer superpose on the Raman spectra (211 and 221). These experimental curves illustrate the effect of the SRS measurement artifacts in regions where the intensity of the molecular vibrations is low.

The present invention provides an original method for detecting a resonant non-linear optical signal of SRS type induced in a sample, which allows the sought-after useful SRS signal to be increased and artifacts, especially that resulting from the cross Kerr effect, to be removed, including in samples formed from scattering biological media.

SUMMARY OF THE INVENTION

According to a first aspect, the invention relates to a device for detecting a resonant non-linear optical signal of Stimulated Raman Scattering (SRS) type induced in a sample. The device comprises:

electro-optical means for making interact in the sample, at a first modulation frequency, trains of light pulses of angular frequencies $\omega_1$ and $\omega_2$ and, at a second modulation frequency, trains of light pulses of angular frequencies $\omega_2$ and $\omega_3$, such that $\omega_2-\omega_1=\omega_3-\omega_2=\Omega_R$ where $\Omega_R$ is a molecular vibrational resonant angular frequency of the sample;

means for synchronous detection at the first and second modulation frequencies of non-linear optical signals resulting from the interaction of the light pulses in the sample; and electronic processing means making it possible to obtain, from electronic signals resulting from the synchronous detection, a signal characterizing the molecular vibrational resonance of the sample.

Thus, this novel device employs three exciting beams, at three preset wavelengths, the pairwise interactions of which in the sample at the first and second modulation frequencies allow both an SRL process and an SRG process to be generated at the same time, the beam of intermediate wavelength serving alternatively as pump beam or Stokes beam in each of the processes. The modulation frequencies may be identical or different depending on the embodiment. In both cases, synchronous detection at the modulation frequency or frequencies of the non-linear optical signals resulting from the interactions of the two processes allows artifacts to be suppressed and the useful SRS signal to be multiplied by two.

The means for making the pulse trains interact in the sample advantageously comprise means for focusing the pulse trains onto a common focusing volume, making it possible to obtain energy densities high enough to generate the non-linear optical effects in the sample.

The device described may be at least partially fibered. The Applicant has shown that the detection method implemented furthermore allows artifacts due to non-linear effects generated in the fiber to be suppressed.

One application of such a device is vibrational Raman imaging, and especially microscopic imaging. The device may then comprise means for moving this focusing volume relative to the sample in order to carry out the imaging.

Another application of the described device is Raman spectroscopy. The device may for example comprise means for varying the angular frequencies $\omega_1$ and $\omega_3$ of the pulse trains that interact in the sample, allowing the molecular vibrational resonant angular frequency $\Omega_R$ of the sample that it is desired to study to be varied.

One application of the described device is hyperspectral Raman imaging, allowing SRS images of the sample at various molecular vibrational resonant angular frequencies $\Omega$ to be produced.

Whether for imaging or spectroscopy, the synchronous detection means comprise optical means for detecting the non-linear optical signals resulting from the interaction of the pulse trains in the sample, the optical detection possibly being carried out in a forward detection mode, in a back (or epi) detection mode or in an endoscopic detection mode, especially for the study of molecular vibrations in deep layers of a biological sample.

As a first variant of the described device, at least one of the pulse trains is amplitude modulated.

In a first embodiment, the electro-optical means comprise a source for emitting trains of pulses at the angular frequencies $\omega_1$, $\omega_2$ and $\omega_3$, and means for amplitude modulating the trains of pulses at the angular frequencies $\omega_1$ and $\omega_3$ at the first and second modulation frequencies, respectively.

The trains of pulses at the angular frequencies $\omega_1$ and $\omega_3$ are for example amplitude modulated at the same modulation frequency but in phase opposition. In this case, the trains of light pulses of angular frequencies $\omega_1$ and $\omega_2$, on the one hand, and the trains of light pulses of angular frequencies $\omega_2$ and $\omega_3$, on the other hand, interact in the sample in alternation at the modulation frequency. The synchronous detection means for example comprise an optical detector of the pulses issued from the sample at the angular frequency $\omega_2$ and synchronous, analog or digital detection of the electrical signal issued from the optical detector at the modulation frequency. The signal issued from the synchronous detection characterizes the molecular vibrational resonance of the sample. The electronic processing means allow this signal to be extracted and then exploited.

Alternatively, the trains of pulses at the angular frequencies $\omega_1$ and $\omega_3$ are amplitude modulated at two separate modulation frequencies that are not multiples of each other. In this case, synchronous detection of the pulses issued from the sample at the angular frequency $\omega_2$ is carried out at each of the modulation frequencies. The signals generated by the synchronous detection are processed to extract the signal characterizing the molecular vibrational resonance of the sample.

In a second embodiment, the first and second modulation frequencies are identical, and the electro-optical means comprise a source for emitting trains of pulses at the angular frequencies $\omega_1$, $\omega_2$ and $\omega_3$, and means for amplitude modulating the train of pulses at the angular frequency $\omega_2$ at the modulation frequency. In this case, synchronous detection at the modulation frequency is carried out for the pulses issued from the sample at the angular frequency $\omega_1$, on the one hand, and the pulses issued from the sample at the angular frequency $\omega_3$, on the other hand. The signals generated by each of the synchronous detections are processed to extract the signal characterizing the molecular vibrational resonance of the sample.

As a second variant of the described device, a delay line is introduced on the path of at least one of the pulse trains and a modulation of the time delay between the pulse trains is carried out.

More precisely, the first and second modulation frequencies being identical, the electro-optical means may comprise a source for emitting trains of pulses at the angular frequencies $\omega_1$, $\omega_2$ and $\omega_3$, and at least one delay line making it possible to generate between the trains of pulses at the angular frequencies $\omega_1$ and $\omega_3$ and the trains of pulses at the angular frequency $\omega_2$, a time delay modulated at the modulation frequency. In this case, as in the case of the trains of pulses amplitude modulated in phase opposition, trains of light pulses of angular frequencies $\omega_1$ and $\omega_2$, the one hand, and trains of light pulses of angular frequencies $\omega_2$ and $\omega_3$, on the other hand, interact in the sample in alternation at the modulation frequency.

Whether in the first variant (amplitude modulation) or in the second variant (time delay modulation), the pulses may for example be spectrally narrow picosecond pulses with angular frequencies centered on the angular frequencies $\omega_1$ and $\omega_2$ and $\omega_3$, or as a variant frequency chirped pulses with angular frequencies centered on the angular frequencies $\omega_1$ and $\omega_2$ and $\omega_3$.

In the case of picosecond pulses, the pulse trains are for example emitted by a picosecond laser source comprising a master laser emitting trains of pulses of angular frequency $\omega_2$ and an OPO laser emitting trains of pulses of angular frequencies $\omega_1$ (Idler) and $\omega_3$ (Signal).

In the case of frequency chirped pulses, the pulse trains are for example obtained by a femtosecond laser source comprising a master laser and an OPO, the pulses being spread by a time stretcher.

In the case of frequency chirped pulses, the emitting source may furthermore comprise a delay line allowing an identical time shift to be generated between the pulses at the angular frequencies $\omega_1$ and $\omega_2$, on the one hand, and the pulses at the angular frequencies $\omega_2$ and $\omega_3$, on the other hand, the variation in the time shift allowing the molecular vibrational resonant frequencies of the sample to be probed.

In the second variant of the described device (time delay modulation), the emitting source may comprise a generator of trains of frequency chirped pulses centered on the angular frequency $\omega_2$, and a dichroic beam splitter making it possible to separate pulses centered on the angular frequency $\omega_2$, on the one hand, and pulses centered on the angular frequencies $\omega_1$ and $\omega_3$, respectively, on the other hand. A time delay modulated at the modulation frequency may then be introduced, as described above, between the trains of pulses at the angular frequencies $\omega_1$ and $\omega_3$ and the trains of pulses at the angular frequency $\omega_2$.

According to a second aspect, the invention relates to a method for detecting a resonant non-linear optical signal of Stimulated Raman Scattering (SRS) type induced in a sample, implemented by the device described according to the first aspect and all of its variants or embodiments.

BRIEF DESCRIPTION OF THE DRAWINGS

Other advantages and features of the invention will become apparent on reading the description, which is illustrated by the following figures:

FIG. 2 (already described), schematic of a prior-art SRS microscope;

FIGS. 5A to 5C, a schematic illustration of the interactions in the sample, according to the first variant;

FIGS. 7A to 7D, schematics illustrating variants of the device shown in FIG. 4, for front, back (or epi), and front fibered detection modes and for an endoscopic detection mode, respectively;

FIGS. 8A to 8C, schematics showing first experimental results obtained with a non-scattering sample, using a device such as shown in FIG. 4;

FIGS. 9A to 9F, schematics showing second experimental results obtained with a scattering sample, using a device such as shown in FIG. 4;

FIGS. 10A to 10C, schematics showing third experimental results obtained with a sample formed from a biological tissue, using a device such as shown in FIG. 4;

FIGS. 11A and 11B, two other example devices illustrating variants of the present invention;

FIGS. 14A to 14C, a schematic illustration of the interactions in the sample, according to the variant shown in FIG. 13;

FIGS. 16A, 16B, schematics illustrating one embodiment of a source of trains of spread spectrum pulses;

FIGS. 17A to 17C, a schematic illustration of the interactions in the sample, according to a first variant (amplitude modulation), with spread spectrum pulses;

FIGS. 21A to 21C, a schematic illustration of the interactions in the sample, in the example in FIG. 20.

DETAILED DESCRIPTION

In the figures, identical elements are indicated by the same references.

Figure 1A:
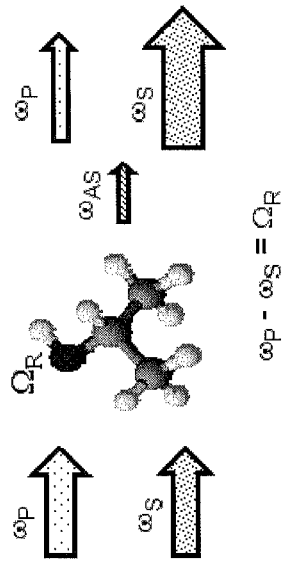
FIGS. 1A and 1B (already described), principle of Stimulated Raman Scattering (SRS)
Figure 1B:
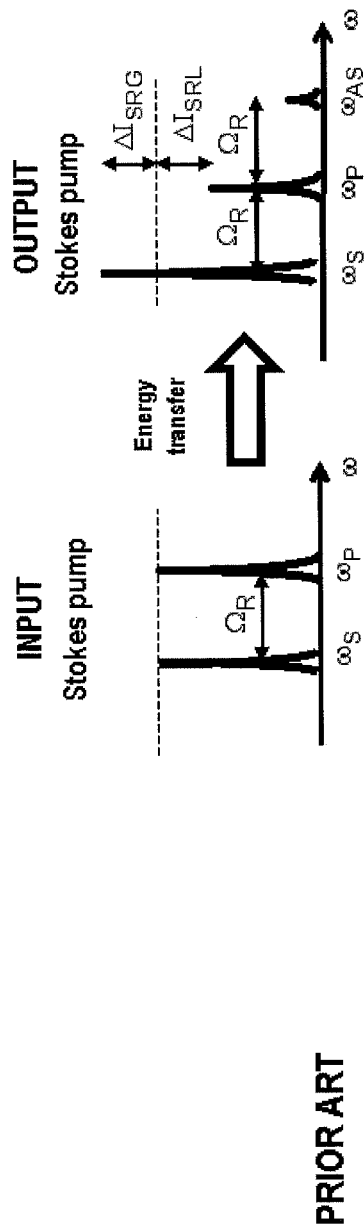
Figure 3A:
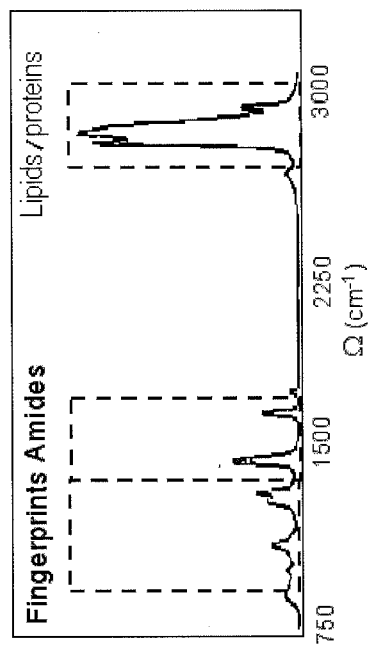
FIGS. 3A to 3D (already described), example Raman spectrum for a human (skin) tissue sample and comparative spectral measurements obtained by prior-art CARS, SRS and Raman micro-spectroscopy in three spectral regions of interest.
Figure 3D:
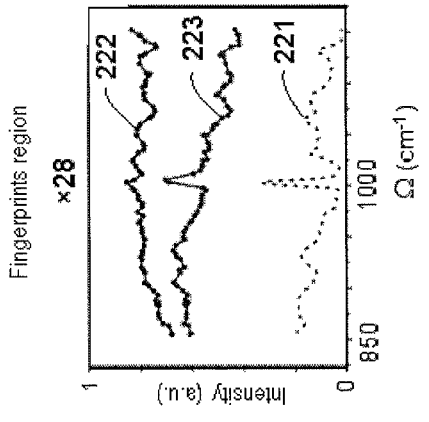
Figure 3C:
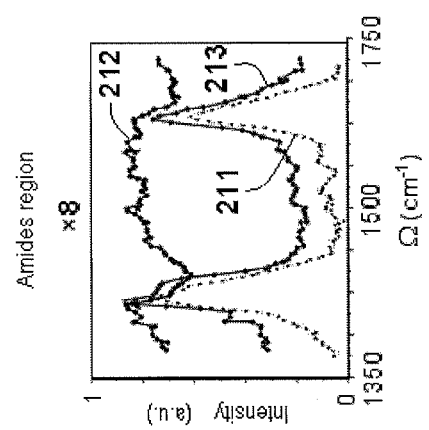
Figure 3B:
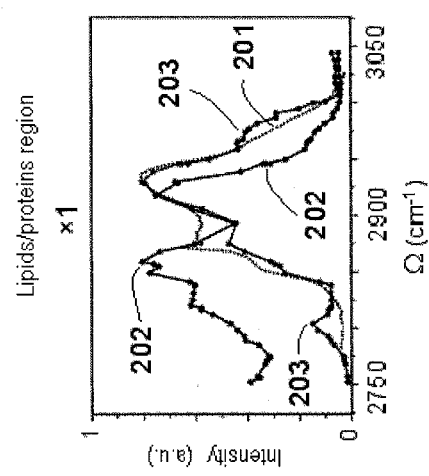
Figure 4:
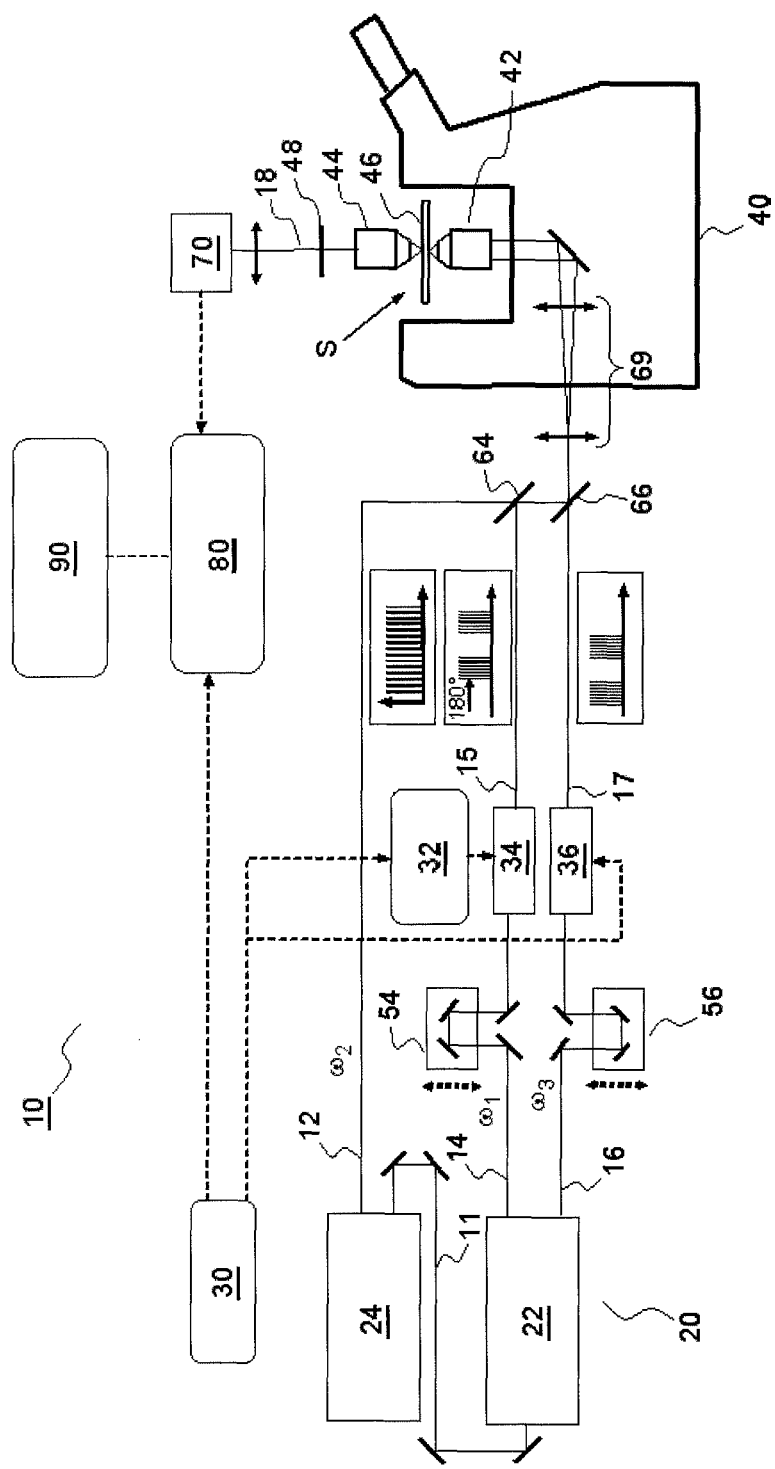
FIG. 4, embodiment of an SRS detection device according to a first example of a first variant of the present invention (amplitude modulation)

FIG. 4 shows an example of a device for detecting a non-linear resonant SRS optical signal according to one variant of the present invention, implementing amplitude modulation.

The detection device 10 comprises a source 20 for emitting trains of pulses centered on the angular frequencies $\omega_1$, $\omega_2$ and $\omega_3$, such that $\omega_2-\omega_1=\omega_3-\omega_2=\Omega_R$ where $\Omega_R$ is a molecular vibrational resonant frequency that it is sought to analyze in a sample S. The pulses are for example picosecond pulses, of a few $cm^{-1}$ in spectral width, or may be frequency chirped pulses as will be described in more detail below. Typically, the trains of pulses for example comprise pulses of a few picoseconds, emitted at rates of a few tens of MHz, for example about 80 MHz, for a length of time of about one microsecond.

According to one variant, the emitting source 20 comprises a laser system consisting of a master laser 24 emitting trains 12 of pulses at the angular frequency at, and an OPO (optical parametric oscillator) laser 22 receiving, from the master laser, frequency-doubled pulses 11 suitable for parametric generation of the Signal and Idler within the OPO. This results in trains 14 and 16 of pulses at tunable angular frequencies $\omega_1$ and $\omega_3$ corresponding to the Idler and the Signal, respectively. The "Laser" beam 12 emitted directly by the master laser 24 and the "Idler" 14 and "Signal" 16 beams emitted by the OPO laser 22 can be directly exploited in SRS imaging according to the present description. Specifically, the parametric generation mechanism of the OPO is such that the angular frequencies of the Laser ($\omega_2$), Signal ($\omega_3$) and Idler ($\omega_1$) pulses respect the condition $\omega_2-\omega_1=\omega_3-\omega_2=\Omega$, where $\Omega$ may be set to the angular frequency $\Omega_R$ of interest by changing the parameters of the OPO. Thus, the wavelength of the pulses 12 being about 1064 nm, the wavelength of the frequency-doubled pulses 13 is about 532 nm, and the wavelengths of the Idler and Signal pulses are tunable between about 1150 to 2450 nm and about 690 to 990 nm, respectively. When the three trains 14, 12, 16 of pulses at the angular frequencies $\omega_1$, $\omega_2$ and $\omega_3$ interact in the sample, the Signal beam plays the pump role in the interaction of the Laser/Signal pulses whereas the Laser beam plays the Stokes role, and the Idler beam plays the Stokes role in the interaction of the Laser/Idler pulses whereas the Laser beam plays the pump role.

In the example in FIG. 4, in each of the Signal and Idler channels, a delay line (56 and 54, respectively) allows the three pulse trains to be temporally synchronized in order to ensure the temporal overlap thereof in the sample.

In the example in FIG. 4, an amplitude modulation is carried out on each of the Signal and Idler pulse trains, at the same modulation frequency but in phase opposition, making it possible to make the trains of light pulses of angular frequencies $\omega_1$ and $\omega_2$ and the trains of light pulses of angular frequencies $\omega_2$ and $\omega_3$, interact in alternation in the sample at the modulation frequency. In other words, for a given time period T only the pulses at the angular frequencies $\omega_1$ and $\omega_2$ interact, and in the following time period, only the pulses at the angular frequencies $\omega_2$ and $\omega_3$ interact, the period T being given by the inverse of the modulation frequency. The Signal and Idler pulse trains are for example both modulated by an acousto-optic modulator (36, 34, respectively). The modulation signal of the acousto-optic modulator 36 of a frequency $f_1$, advantageously higher than 1 MHz, typically between 1 and 40 MHz, is delivered by a low-frequency generator 30. The modulation signal of the acousto-optic modulator 34 of same frequency $f_1$ comes from the same source but is offset in phase by means of an electronic delay generator 32 so that the Signal and Idler pulse trains are modulated in phase opposition.

The pulse trains 15 and 17 modulated in phase opposition (respectively at angular frequencies $\omega_1$ and $\omega_3$) are combined with the train of Laser pulses at the angular frequency $\omega_2$, for example by means of dichroic mirrors 64, 66 then focused onto a common focusing volume in the sample S by means of a microscope objective 42, for example a microscope objective of a numeric aperture NA=0.45 that is achromatic in the near infrared domain (~700-1300 nm) An objective 44 having a larger numerical aperture, for example NA=0.60, allows the pulse trains issued from the sample to be collected without diaphragming them. The train 18 of pulses at the angular frequency $\omega_2$ issued from the sample is then filtered by an optical interference filter 48 then detected, for example by a photodiode 70 sensitive at 1064 nm. The modulation signal is then detected by a synchronous detection 80 and the signal issued from the synchronous detection shaped by processing means 90. The synchronous detection means may for example comprise an analog synchronous detection at the modulation frequency $f_1$. Alternatively, the synchronous detection of the signal may be carried out digitally, via digital processing of the signals directly issued from the optical detection. Advantageously, in each of the Signal and Idler channels, a telescope (not shown) of magnification 1 allows the divergence between the Signal and Idler beams to be adjusted in order to optimize their spatial overlap at the focal point of the objective. A telescope 69, for example of magnification 3, allows the diameter of the exciting beams to be increased in order to completely fill the back pupil of the objective. In this case, the exciting numerical aperture is that given by the manufacturer of the objective. The Signal and Idler beams are, for example, excited in their fundamental TEM00 mode so that the electrical and magnetic fields both lie perpendicular to the propagation direction of these signals; the three Laser, Signal and Idler beams are for example linearly polarized with the same polarization direction, enabling optimization of the signal in a uniform medium.

According to one variant, a motorized stage 46 allows the sample to be moved relative to the common focusing volume of the pulse trains in order to form an image of the sample for application of the device to SRS imaging. The focusing and collecting objectives, and the stage 46 are for example arranged in a body of a microscope 40. Alternatively, a system for scanning the exciting beams may be used to move the focusing volume through the sample. In the example of application to SRS imaging, the processing means 90 furthermore allow the sought-typical signal to be extracted as a function of the position in the sample in order to generate an image.

For application of the device to spectroscopy or hyperspectral imaging, it is also possible to vary the angular frequencies $\omega_1$ and $\omega_3$ of the Idler and of the Signal, allowing the SRS signal to be probed as a function of molecular vibrational frequency $\Omega$. The processing means 90 then allow the sought-after characterizing signal to be extracted as a function of the molecular vibrational frequency $\Omega$ to form a spectrum.

FIGS. 5A to 5C and 6 illustrate the principle of a detection method according to a variant of the present description, for example implemented by means of the device shown in FIG. 4, and which will be referred to as the stimulated Raman gain-opposite-loss detection (SRGOLD) method in the rest of the description.

FIG. 5A illustrates the state denoted "state a" in which pulses at the angular frequency $\omega_2$ and pulses at the angular frequency $\omega_1$ superpose for the time period T. In this example, the pulses are short pulses, for example picosecond pulses, typically smaller than 100 ps in length. FIG. 5B illustrates the state denoted "state b" in which pulses at the angular frequency $\omega_2$ and pulses at the angular frequency $\omega_3$ superpose for the same time period T but in alternation with state a. In this example, the difference between the angular frequencies $\omega_2-\omega_1$ and $\omega_3-\omega_2$ is considered to equal $\Omega_R$, where $\Omega_R$ is a resonant angular frequency of a molecular vibrational mode of the sample. By virtue of the method implemented by the device shown in FIG. 4, the states a and b alternate in the sample at the modulation frequency $f_1$, as is illustrated in FIG. 5C.

Figure 6:
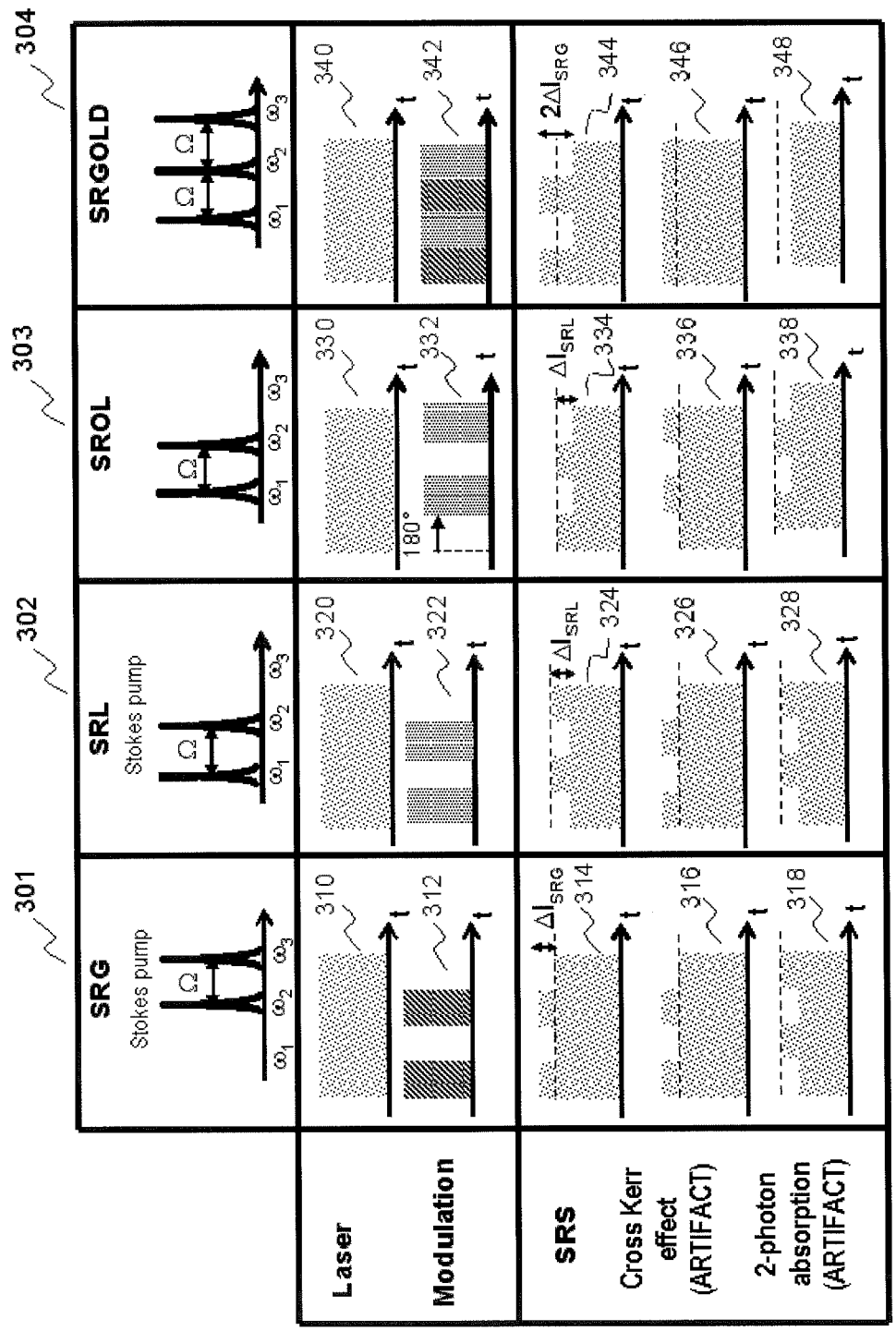
FIG. 6, a table illustrating the signals detected (SRS signals and artifacts) in the example implementation of the device shown in FIG. 4.

FIG. 6 illustrates the physical mechanisms at play during the interaction of the trains of pulses at the angular frequencies $\omega_3$ and $\omega_2$ in the sample ("state b", column 301: "SRG"), during the interaction of the trains of pulses at angular frequencies $\omega_1$ et $\omega_2$ (column 302: "SRL"), during the interaction of trains of pulses at angular frequencies $\omega_1$ and $\omega_2$ phase shifted by 180° relative to state b ("state a", column 303: "SROL"), and the implemented detection (column 304: "SRGOLD").

Consideration is first given (column 301) to the interaction of the unmodulated train (12, FIG. 4) of Laser pulses, the intensity of which is schematically shown as a function of time by the curve 310, with the train of pulses at the angular frequency $\omega_3$, which train is amplitude modulated at the modulation frequency $f_1$ (17, FIG. 4), the intensity of this train being schematically shown as a function of time by the curve 312. In these schematics, only the envelope of the pulse train is shown. In this interaction, the pulses at the angular frequency $\omega_3$ (Signal) play the pump role whereas the Laser pulses at the angular frequency $\omega_2$ play the Stokes role. The latter see, after interaction in the sample, an energy gain (SRG) at the expense of the Stokes pulses, this gain being schematically shown in the curve 314 by the intensity variation $\Delta I_{SRG}$. The curves 316 and 318 illustrate the effects of artifacts due to the cross Kerr effect and to 2-photon absorption, respectively. In this example it is assumed that the cross Kerr effect manifests as a focusing effect that leads to a gain in the intensity of the Laser pulses, which gain is modulated at the modulation frequency $f_1$. The 2-photon absorption manifests as a loss in the intensity of the Laser pulses, at the modulation frequency $f_1$.

Consideration is now given (column 302) to the interaction of the unmodulated train of Laser pulses, the intensity of which is schematically shown as a function of time by the curve 320, with a train of pulses at the angular frequency $\omega_1$, which train is amplitude modulated at the modulation frequency $f_1$, the intensity of this train being schematically shown as a function of time by the curve 322. In this interaction, the pulses at the angular frequency $\omega_1$ (Idler) play the Stokes role whereas the Laser pulses at the angular frequency $\omega_2$ play the pump role. The latter therefore see, after interaction in the sample, an energy loss (SRL) schematically shown in the curve 324 by the intensity variation $\Delta I_{SRL}$. The curves 326 and 328 illustrate the effects of artifacts due to the cross Kerr effect and to 2-photon absorption, respectively. If the pulses at the angular frequency $\omega_3$ create a cross Kerr effect that causes the Laser pulses to focus (curve 316), the pulses at the angular frequency $\omega_1$ also cause the Laser pulses to focus leading to a gain in the intensity of the latter, which gain is modulated at the modulation frequency $f_1$ (curve 326). The 2-photon absorption manifests as above as a loss in the intensity of the Laser pulses, at the modulation frequency $f_1$ (curve 328). Thus, it is observed that when the trains of pulses at angular frequencies $\omega_1$ and $\omega_3$ are amplitude modulated in phase, the induced artifacts are also in phase whereas the SRL and SRG modulations are in phase opposition (compare curves 314 and 324).

Supposing now that the train of Laser pulses at the angular frequency $\omega_2$ (curve 330, column 303) interacts with the train of pulses at the angular frequency $\omega_1$, which train is amplitude modulated in phase opposition relative to the modulation of the train of pulses at the angular frequency $\omega_3$ (curve 332, column 303). In this case, the SRL modulation of the trains of Laser pulses (curve 334) is in phase with the SRG modulation (curve 314) whereas the artifacts induced by the trains of pulses at the angular frequency $\omega_1$ (curves 336, 338) are in phase opposition with those induced by the trains of pulses at the angular frequency $\omega_3$ (curves 316, 318). The method described according to the present variant, baptized SRGOLD for "stimulated Raman gain-opposite-loss detection", thus consists in amplitude modulating the trains of pulses at angular frequencies $\omega_1$ et $\omega_3$ in phase opposition (curves 342, column 304) and in detecting the modulations induced on the unmodulated train of Laser pulses (curve 340) by synchronous detection at the modulation frequency. Under these conditions, the artifacts, in phase opposition, counterbalance (see curves 346, 348 and column 304) and disappear during the synchronous detection. In addition, the SRL and SRG signals are in phase and add during the synchronous detection (curve 344), according to the following expression:

$$\Delta I_{SRGOLD} = \Delta I_{SRG} + \Delta I_{SROL} = \Delta I_{SRG} + \Delta I_{SRL} \times \cos(180°).$$

By neglecting wavelength and assuming that the exciting intensities are equivalent (intensity of pulses at the angular frequency $\omega_1$ incident on the sample identical to the intensity of the pulses at the angular frequency $\omega_3$), it may be deduced that:

$$\Delta I_{SRGOLD} \approx 2\Delta I_{SRG}.$$

The detection device 10 shown in FIG. 4 comprises forward optical detection means and the exciting beams propagate in free space in the device. FIGS. 7A to 7D schematically illustrate a number of variants of the detection device shown in FIG. 4. The schematics are partial, only elements useful to comprehension being shown.

FIG. 7A shows a detection device similar to that in FIG. 4. However, for the sake of simplicity all the elements have not been shown. In particular, the block 36 represents the module allowing the trains of pulses at the angular frequency $\omega_1$ to be amplitude modulated at the modulation frequency $f_1$, and the block 34 represents the module allowing the trains of pulses at the angular frequency $\omega_3$ to be amplitude modulated at the modulation frequency $f_1$, in phase opposition with the modulation of the trains of pulses at the angular frequency $\omega_1$. In the rest of the description, modulation in phase opposition at the frequency $f_t$ is denoted by "$-f_1$".

FIG. 7B shows a partial schematic of a variant of the device shown in FIG. 7A, in which device the optical detection is carried out in a back (or "epi") mode. In this configuration, the focusing objective 42 also acts as the collecting objective, the detected signal being the signal backscattered by the sample. In this variant, the optical detection means may comprise, in addition to the fast detector 70, a half-silvered dichroic plate 65 allowing the trains of pulses at the angular frequency $\omega_2$ to be reflected. By virtue of the detection method according to the present description, the effects of artifacts especially resulting from 2-photon absorption and the optical cross Kerr effect, which induces a modulated diaphragming effect in the objective 42 acting as the collecting objective of the SRS signal, are suppressed as was explained above, whereas the useful SRS signal is multiplied.

FIG. 7C shows a partial schematic of a variant of the device shown in FIG. 7A, in which device the propagation of the exciting beams 12, 15, 17 is carried out in fibered mode, at least partially. In optical microscopy applications for example, it is sought to propagate light beams in the device via optical fiber, especially for reasons of bulk and ease of adjustment of optical components. In the example shown in FIG. 7C, the propagation of the exciting beams is carried out by means of an optical fiber 60 located upstream of the focusing objective 42. The optical fiber is for example a monomode fiber. Objectives 61 and 63 allow the exciting beams to be coupled at the entrance and exit of the fiber, respectively. The detection method described in the present description thus makes it possible not only to limit, as was described above, the effects of artifacts resulting from interaction of the exciting beams in the sample, but also to limit possible measurement artifacts resulting from non-linear effects in the optical fiber 60. Specifically, due to the light intensities propagated in the fiber, non-linear effects such as degenerate four-wave mixing or the cross Kerr effect may appear in the fiber itself and, for the same reasons as those explained above, cause depletion of the Laser pulses at the modulation frequency $f_1$, thus generating a measurement artifact. By modulating the trains of pulses at the angular frequencies $\omega_1$ and $\omega_3$ at the same frequency but in phase opposition, and by using synchronous detection to detect the signal at the angular frequency $\omega_2$, artifacts generated by non-linear effects in the fiber are also suppressed.

Figure 7D:
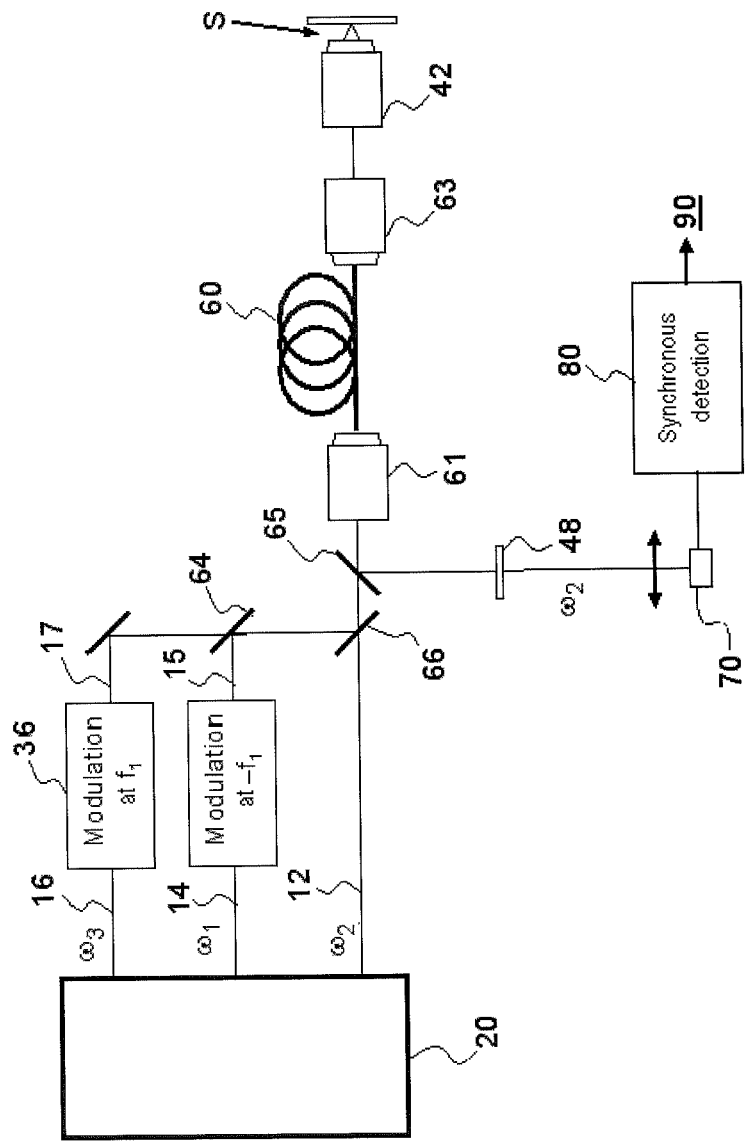

FIG. 7D shows a partial schematic of a variant of the device shown in FIG. 7A, in which device the propagation of the exciting beams 12, 15, 17 is carried out at least partially in fibered mode, and the optical detection is carried out in an endoscopic detection mode. Here, the sample S for example corresponds to deep layers of a biological medium. Detection is carried out in back (or epi) mode. The nonlinear optical signal of interest, at the angular frequency $\omega_2$, backscattered by the sample is transmitted, after passage through the optical fiber 60, by means of a dichroic mirror, to the fast detector 70. In this detection mode, in addition to diaphragming by the objective 42 acting as the collecting objective of the SRS signal, the signal may also be diaphragmed by the optical fiber 60. The method according to the present description allows to overcome all these artifacts, including those resulting from diaphragming by the optical fiber.

FIGS. 8A to 8C show the first experimental results aiming to validate the detection method implemented with a device such as shown in FIG. 4 on non-scattering samples.

FIG. 8A shows three spectra obtained with a receptacle of chlorobenzene, which spectra were produced between 960 and 1120 cm$^{-1}$. In order to ensure the artifact effects due to the cross Kerr effect were observed, a diaphragm was arranged upstream of the detector, this diaphragm being closed such that 50% of the intensity of the Laser pulses at the angular frequency $\omega_2$ was cut. The curves 501, 502, 503 show the spectra produced using the SRG, SROL and SRGOLD modes, respectively, such as described in FIG. 6. More precisely, the SRG-mode curve was obtained by cutting the train of pulses at the angular frequency $\omega_1$, the SROL-mode curve was obtained by cutting the train of pulses at the angular frequency $\omega_3$ and the SRGOLD-mode curve was obtained by making the trains of pulses at the angular frequencies $\omega_1$, $\omega_2$ and $\omega_3$ interact in the receptacle of liquid, the trains of pulses at the angular frequencies $\omega_1$, $\omega_3$ being amplitude modulated in phase opposition. For these experiments, the average optical power of the train of Laser pulses, measured after the combiner 66 (FIG. 4), was set to 90 mW, and the average optical powers of the train of pulses at the angular frequencies $\omega_1$ and $\omega_3$ were set to 50 mW so that the cross Kerr effect generated by the pulses at the angular frequency $\omega_1$, and considered as the main component of the artifacts, exactly counterbalanced the cross Kerr effect generated by the pulses at the angular frequency $\omega_3$. This adjustment may be carried out by zeroing the SRGOLD signal off resonance, for example at $\Omega$=960 cm$^{-1}$. As may be seen from the curve 501, the SRG spectrum, obtained by synchronous detection at the frequency $f_1$, of the SRS signal resulting from the interaction between the train of Laser pulses ($\omega_2$) and the train of Signal pulses ($\omega_3$), the latter train being amplitude modulated at the frequency $f_1$, contains a parasitic negative offset corresponding to the cross Kerr effect, the Kerr effect manifesting here as an effect causing the Laser beam to defocus. As expected, the SROL spectrum (curve 502), obtained by synchronous detection, at the frequency $f_1$, of the SRS signal resulting from the interaction between the train of Laser pulses ($\omega_2$) and the train of Idler pulses ($\omega_1$), the latter train being amplitude modulated at the frequency $f_1$ but in phase opposition, contains an offset, due to the cross Kerr effect, of opposite sign to that observed in the SRG configuration. In SRGOLD mode (curve 503), synchronous detection, at the frequency $f_1$, of the Laser signal allows the effect of artifacts due to the cross Kerr effect, which have opposite signs and counterbalance over the entire spectral range, to be suppressed. These experiments allowed it to be confirmed that with the SRGOLD method thus described it is possible to completely suppress the cross Kerr effect in a uniform medium.

FIG. 8C shows pictures that validate the SRGOLD method described above. For these experiments, a series of images were taken, at resonance ($\Omega$=1003 cm$^{-1}$) and off resonance ($\Omega$=930 cm$^{-1}$), of a sample such as illustrated in FIG. 8B, the sample containing 20 µm-diameter polystyrene beads 413 submerged in an index liquid 411, having a refractive index of 1.54, located between two glass slides 410, 412. This experiment was carried out, as above, with a diaphragm positioned upstream of the detector and partially closed in order to maximize detection of the cross Kerr effect. The average optical power of the train of Laser pulses was about 160 mW, and that of the train of Signal pulses (angular frequency $\omega_3$) about 70 mW. Artifacts were minimized on the liquid by adjusting the average optical power of the train of Idler pulses (angular frequency $\omega_1$) to about 30 mW. FIG. 8C shows images of a polystyrene bead at resonance in SRG (511), SROL (512) and SRGOLD (513) modes, respectively, compared to an image taken with an unmodulated Laser beam (514). FIG. 8C shows these same images off resonance (images 521 to 524, respectively). The "Laser" image is a reference image that allows noise to be evaluated, this image being obtained by cutting the trains of pulses at the angular frequencies $\omega_1$, $\omega_3$. Artifacts are clearly present in the SRG and SROL measurements both at resonance and off resonance, these artifacts having opposite signs. At resonance, in the SRGOLD image, the contribution of the liquid disappears, and the SRS signal coming from the bead is more intense than in the SRG and SROL images (the two contributions are summed). Off resonance, it may be seen that the artifacts have considerably decreased relative to the SRG and SROL images. The contribution of the liquid has completely disappeared. Only a slight residual artifact (<10% relative to the artifacts of the SRG image) is measured for the bead.

FIGS. 9A to 9D show experimental results obtained for a scattering sample the characteristics of which are closer to those of a biological tissue.

FIG. 9A shows the sample, which was identical to that in FIG. 8B except that a scatterer 414 was provided, for example a strip of adhesive tape was placed on the receptacle containing the polystyrene beads submerged in the index liquid. This time no diaphragm was present in the device and the numerical aperture of the collecting objective 44 was chosen to be higher than that of the focusing objective 42. The images 505 and 506 (FIG. 9B) show the images of the Laser beam obtained at the back pupil of the collecting objective, in the absence of the scatterer and in the presence of the scatterer, respectively. The dashed white circle indicates the size of the pupil of the objective. In the absence of the scatterer, the Laser beam was not diaphragmed because the collecting numerical aperture was higher than that of the exciting numerical aperture. In contrast, the presence of the scatterer broadened the angular spectrum of the Laser beam exiting from the sample. The pupil of the collecting objective then played the role of a diaphragm. Thus, some of the energy (about 12.5%) was blocked. FIGS. 9C and 9D show images of a polystyrene bead, at resonance (531 to 534) and off resonance (541 to 544), for SRG, SROL, SRGOLD and Laser configurations. To obtain these images, the powers were about 50 mW (Laser), 50 mW (Idler) and 60 mW (Signal). The color scale was chosen to highlight artifacts. The SRG (531, 541) and SROL (532, 542) images exhibit the detection of the cross Kerr effect due to scattering by the sample. As in the above experiments, it may be seen in the SRGOLD images (533, 543) that the contribution of the liquid has disappeared and that the contribution of the bead off resonance has greatly decreased.

It will be noted that the Raman line studied here ($\Omega$=1003 cm$^{-1}$) is extremely intense relative to the artifacts. FIG. 9F shows a series of 50 μm×50 μm images taken for the same scattering sample as above at $\Omega$=1034 cm$^{-1}$ (images 551 to 554) and at $\Omega$=1041 cm$^{-1}$ (images 561 to 564). The latter frequency is shifted slightly relative to the maximum of the Raman line at 1034 cm$^{-1}$ (see the Raman spectrum 510 of polystyrene shown in FIG. 9E) and thus allows the case of a Raman line of comparable intensity to the artifacts to be simulated. For this frequency, the contrast of the polystyrene beads in the SRG and SROL images (561, 562) is low because the measurement is dominated by the cross Kerr effect. In contrast, the beads have a good contrast in the SRGOLD image (563) because artifacts were decreased and the SRS signal was about two times stronger than for the SRG or SROL images. It will be noted that the various images are corrupted with the same amount of noise due to the Laser beam and due to electronic noise.

Figure 10B:
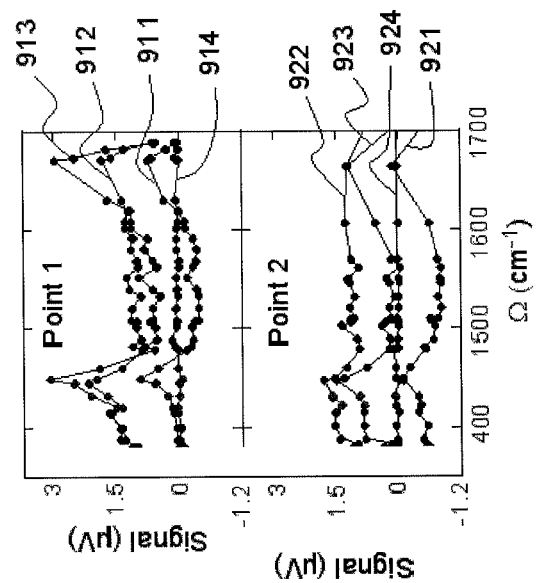
Figure 10A:
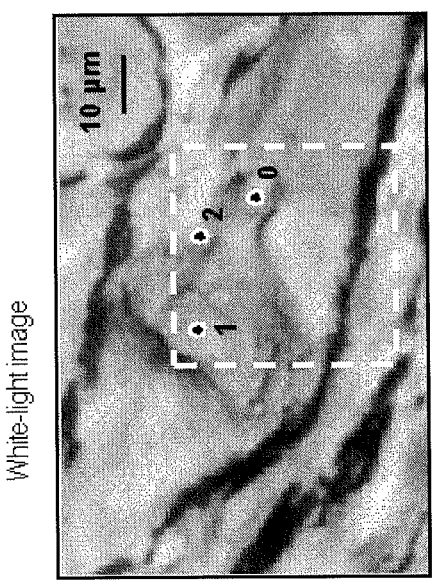

FIGS. 10A to 10C show the first results obtained for biological tissues by virtue of the SRGOLD method described according to the present variant. The biological tissue was mouse skin (20 μm-thick sample). FIG. 10A shows a white-light image of the studied zone. Compensation for artifacts was carried out off resonance (1550 cm$^{-1}$) at the point denoted 0 in the white-light image. This point was chosen arbitrarily. The average optical powers were about 33 mW (Laser), 40 mW (Idler) and 86 mW (Signal). FIG. 10B shows the SRG (911, 921), SROL (912, 922), SRGOLD (913, 923) spectra and the Laser reference (914, 924) in the amide spectral range (1350-1700 cm$^{-1}$), the spectra being measured at the points 1 and 2 indicated on the white-light image, respectively. In both cases, the SRG and SROL measurements were of opposite signs at off-resonance frequencies (about 1550 cm$^{-1}$), thereby confirming the presence of artifacts. In the SRGOLD spectra, the influence of the artifacts was decreased.

FIG. 10C shows images taken at the resonance of the II amides (1450 cm$^{-1}$) and off resonance (1550 cm$^{-1}$) for the various configurations: SRG, SROL, SRGOLD and Laser (curves denoted 571 to 574 at resonance and 581 to 584 off resonance, respectively). The imaged zone is indicated by the dashed line in the white-light image shown in FIG. 10A. At resonance, it is difficult to identify structures in the SRG (571) and SROL (572) images, whereas a structure similar to the white-light image may be seen in the SRGOLD image (573). Off resonance, overall the SRGOLD image (583) has a better null signal than the SRG and SROL images. These experiments show, in biological tissues, the influence of scattering on SRS measurements. The SRGOLD technique allows a better spatial and spectral contrast and a better specificity to be obtained.

The method described by means of the device in FIG. 4 or 7A has the advantage of being simple to implement as synchronous detection at a modulation frequency can be carried out for an optical signal (train of pulses at the angular frequency $\omega_2$), and as this implementation uses common commercially available components.

Figure 12A:
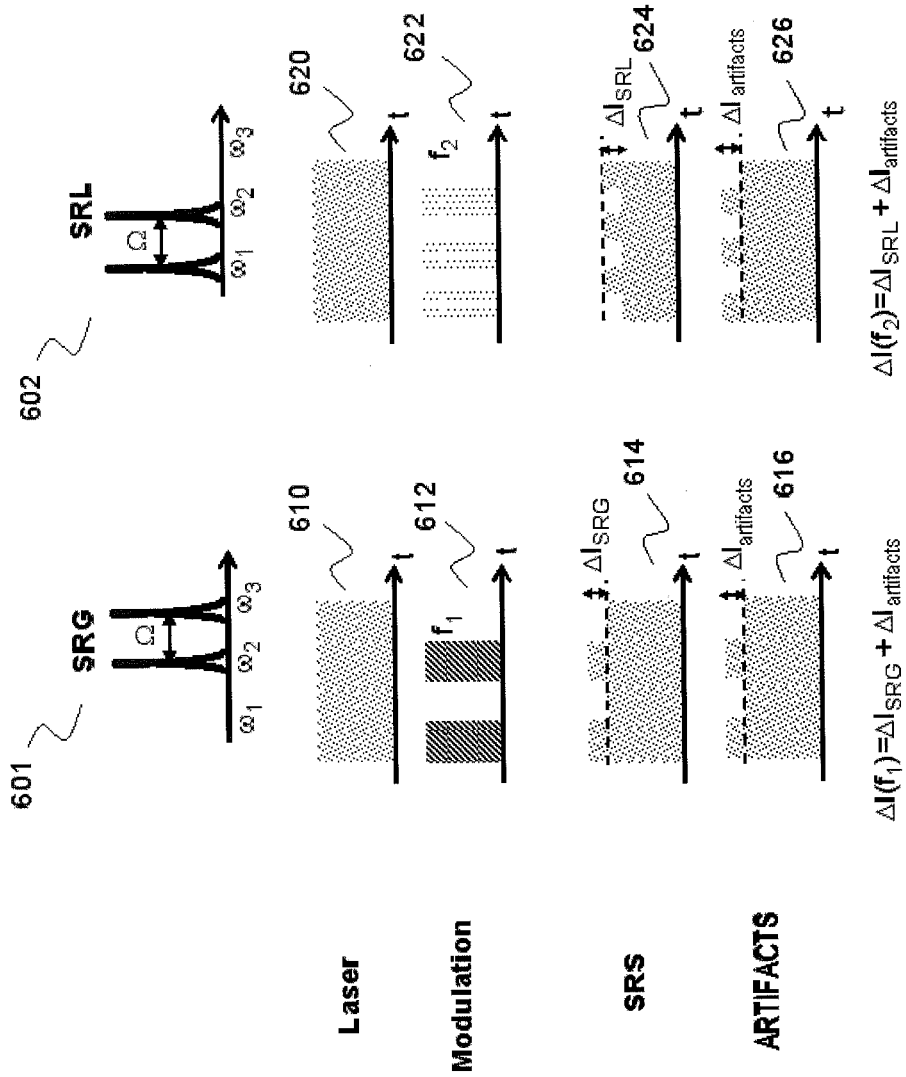
FIGS. 12A and 12B, tables illustrating the signals detected (SRS signals and artifacts) in the example implementations of the devices shown in FIGS. 11A and 11B, respectively.
Figure 12B:
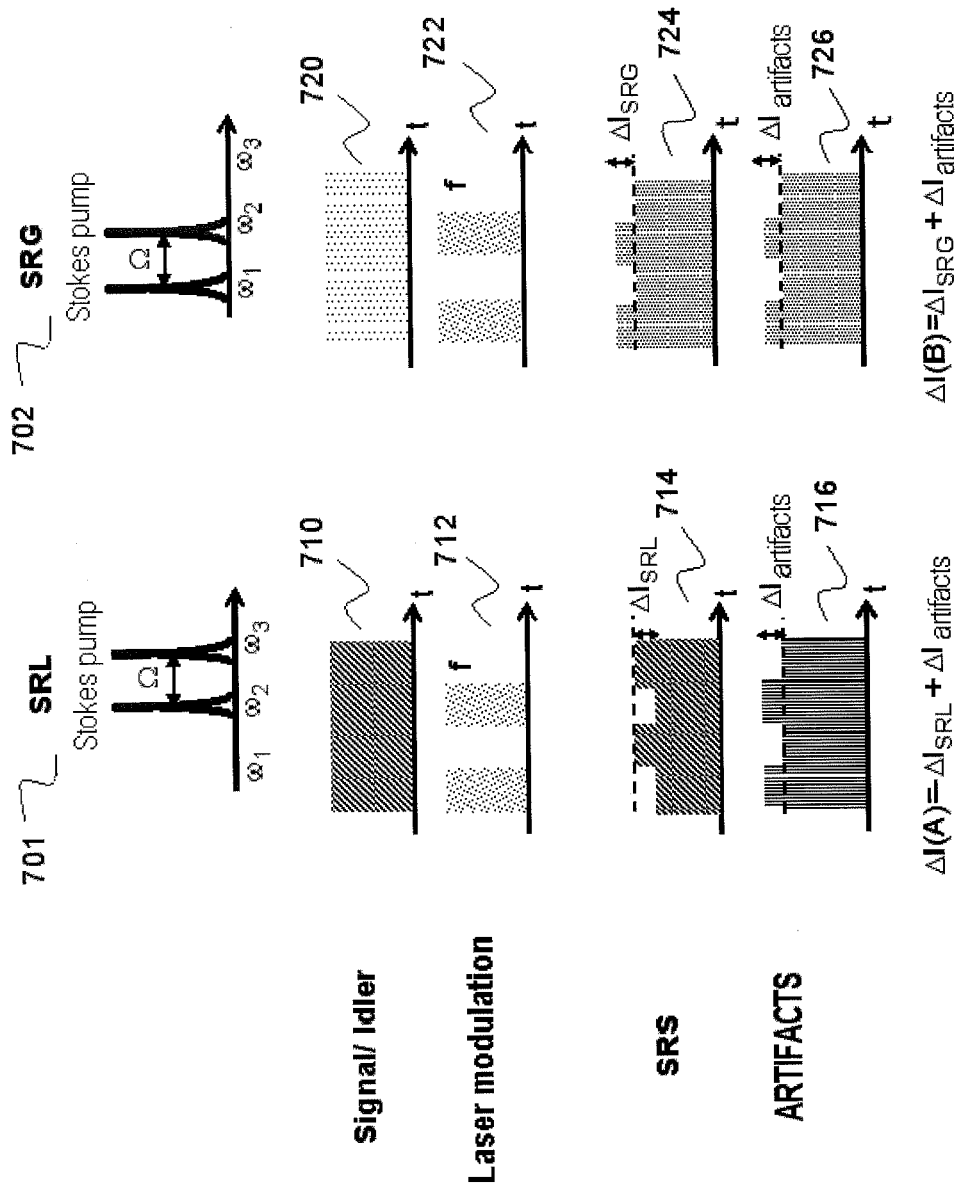

FIGS. 11A and 11B illustrate two variants of the device shown in FIGS. 4 and 7A. FIGS. 12A and 12B show tables illustrating the signals detected (SRS signals and artifacts) in the example implementations of the devices shown in FIGS. 11A and 11B, respectively.

In the example in FIG. 11A, trains 14 and 16 of pulses at the angular frequencies $\omega_1$ (Idler) and $\omega_3$ (Signal) are amplitude modulated at separate modulation frequencies $f_2$ and $f_1$ that are not multiples of each other in order to form modulated pulse trains 15, 17. The train 12 of pulses at the angular frequency $\omega_2$ (Laser) is not modulated. Therefore, trains of pulses at the angular frequencies $\omega_2$ and (modulated) $\omega_1$, on the one hand, and the trains of pulses at the angular frequencies $\omega_2$ and (modulated) $\omega_3$, on the other hand, interact in the sample. As above, pulses at the angular frequency $\omega_2$ issued from the sample are detected. During the interaction of the Laser/Signal pulses, the process involved is an SRG process, as illustrated in column 601 of FIG. 12A. Curve 610 shows the unmodulated train of Laser pulses, and curve 612 the train of pulses at the angular frequency $\omega_3$, which train is modulated at the frequency $f_1$. In these curves, only the envelope of the pulse trains is shown. The SRS signal resulting from the interaction of these two pulse trains exhibits a positive intensity variation $\Delta I_{SRG}$ that is modulated at the modulation frequency $f_1$ (curve 614). The artifacts (the contribution resulting from the Kerr effect is assumed to be preponderant) exhibit an intensity variation $\Delta I_{Artifacts}$ that is modulated at the same modulation frequency $f_1$ (curve 616) and that is assumed to be positive. Therefore, by synchronous detection at the modulation frequency $f_1$ a signal $\Delta I(f_1)$ is obtained such that:

$$\Delta I(f_1) = \Delta I_{SRG} + \Delta I_{Artifacts}$$

Moreover, during the interaction of the Laser/Idler pulses, the process involved is an SRL process, as illustrated in column 602 of FIG. 12A. The curve 620 shows the unmodulated train of Laser pulses, the curve 622 the train of pulses at the angular frequency $\omega_1$, which train is modulated at the frequency $f_2$. The SRL signal resulting from the interaction of these two pulse trains exhibits a negative intensity variation $-\Delta I_{SRL}$ that is modulated at the modulation frequency $f_2$ (curve 624). The artifacts exhibit an intensity variation $\Delta I_{Artifacts}$ that is modulated at the same modulation frequency $f_2$ (curve 626) and that has the same sign as the intensity variation due to the artifacts in the SRG process. By adjusting the average optical powers of the pulse trains incident on the sample, it is possible to obtain an intensity variation $\Delta I_{Artifacts}$ of the same value in both the SRG and the SRL process. Therefore, by synchronous detection at the modulation frequency $f_2$ a signal $\Delta I(f_2)$ is obtained such that:

$$\Delta I(f_2) = -\Delta I_{SRL} + \Delta I_{Artifacts}$$

Electronic processing of the signals issued from the synchronous detection at the modulation frequency $f_1$ and from the synchronous detection at the modulation frequency $f_2$ then allows, by subtraction, an amplified useful SRS signal to be obtained, whereas the signals due to the artifacts cancel out. This method may also be used to determine the contribution the artifacts make to the total signal by adding the signals issued from the synchronous detections, allowing another piece of contrast information to be obtained.

FIG. 11B shows another variant in which the trains 14 and 16 of pulses at angular frequencies $\omega_1$ (Idler) and $\omega_3$ (Signal) are not modulated, the train 12 of pulses at the angular frequency $\omega_2$ (Laser) instead being amplitude modulated at a frequency f. Therefore, trains of pulses at the angular frequencies $\omega_1$ and (modulated) $\omega_2$, on the one hand, and trains of pulses at the angular frequencies $\omega_3$ and (modulated) $\omega_2$, on the other hand, interact in the sample. In contrast to the methods described above, in this example it is the pulses issued from the sample at the angular frequency $\omega_1$, on the one hand, and the pulses issued from the sample at the angular frequency $\omega_2$, on the other hand, that are detected. Thus, the detection means comprise two channels separated by a dichroic mirror 68. In a first channel, a filter 47 allows only pulses at the angular frequency $\omega_1$ to be transmitted, which pulses are detected by means of a fast optical detector 71. In the second channel, a filter 49 allows pulses at the angular frequency $\omega_3$ to be transmitted, which pulses are also detected by means of a fast optical detector 72. In each channel, synchronous detection of the signals issued from the optical detectors is carried out at the modulation frequency f. During the interaction of the Laser/Signal pulses in the sample, the process involved is an SRL process, as illustrated in column 701 of FIG. 12B. The curve 710 shows the unmodulated train of pulses at the angular frequency $\omega_3$, and curve 712 the train of Laser pulses, the latter train being modulated at the frequency f. The SRL signal measured on the pulses at the angular frequency $\omega_3$ (pump) and resulting from the interaction of these two pulse trains exhibits a negative intensity variation $-\Delta I_{SRL}$ that is modulated at the modulation frequency f (curve 714). As above, the artifacts exhibit an intensity variation $\Delta I_{Actifacts}$ that is modulated at the same modulation frequency f (curve 716). Therefore, by synchronous detection at the modulation frequency f a signal $\Delta I(A)$ is obtained such that:

$$\Delta I(A) = -\Delta I_{SRL} + \Delta I_{Artifacts}$$

Moreover, during the interaction of the Laser/Idler pulses, the process involved is an SRG process, as illustrated in column 702 of FIG. 12B. The curve 720 shows the train of pulses at the angular frequency $\omega_1$, which train is unmodulated, and curve 722 the train of Laser pulses at the angular frequency $\omega_2$, which train is modulated at the frequency f. This time, the SRG signal measured from the (Stokes) pulses at the angular frequency $\omega_1$, and resulting from the interaction of these two pulse trains, exhibits a positive intensity variation $\Delta I_{SRG}$ that is modulated at the modulation frequency f (curve 724). The artifacts exhibit an intensity variation $\Delta I_{Artifacts}$ that is modulated at the same modulation frequency f (curve 726) and that is of the same sign as the intensity variation due to the artifacts in the SRL process. As above, by adjusting the average optical powers of the pulse trains incident on the sample, it is possible to obtain an intensity variation $\Delta I_{Artifacts}$ of the same value in both the SRG and the SRL process. Therefore, by synchronous detection at the modulation frequency f a signal $\Delta I(B)$ is obtained such that:

$$\Delta I(B) = \Delta I_{SRG} + \Delta I_{Artifacts}$$

Electronic processing of the signals issued from the synchronous detections in each of the channels, at the modulation frequency f, then allows, by subtraction, an amplified useful SRS signal to be obtained, whereas the signals due to the artifacts cancel out. This method may also be used to determine the contribution the artifacts make to the total signal by adding the signals issued from the synchronous detections.

The examples described up to now have implemented amplitude modulation of one or two pulse trains. The method according to the present description may also be implemented by means of modulation of a time delay introduced between the train of Laser pulses at the angular frequency $\omega_2$ and the trains of pulses at the angular frequencies $\omega_1$ and $\omega_3$.

Figure 13:
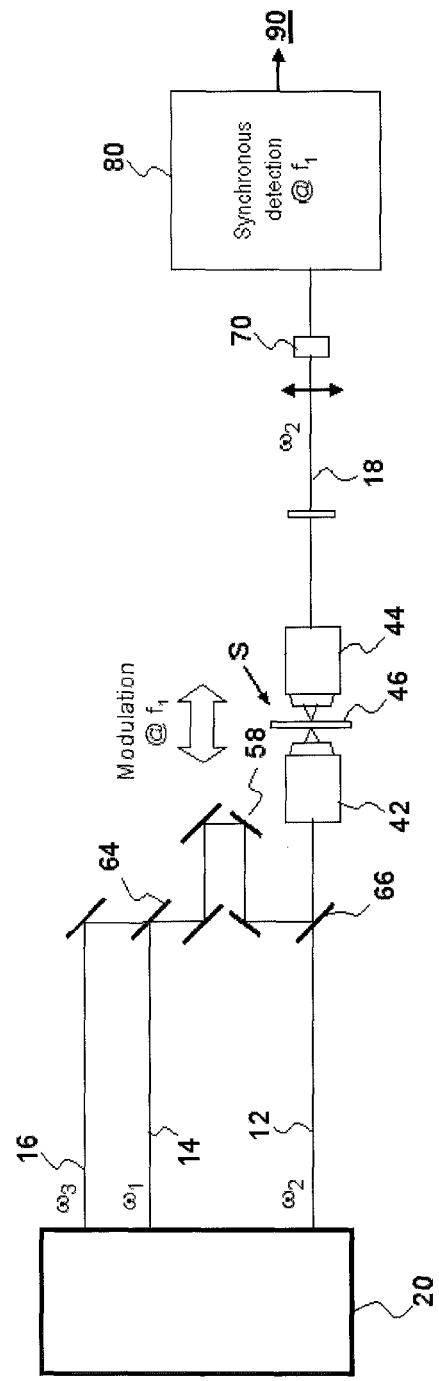
FIG. 13, one embodiment of an SRS detection device according to another variant of the present invention (time delay modulation)
Figure 15:
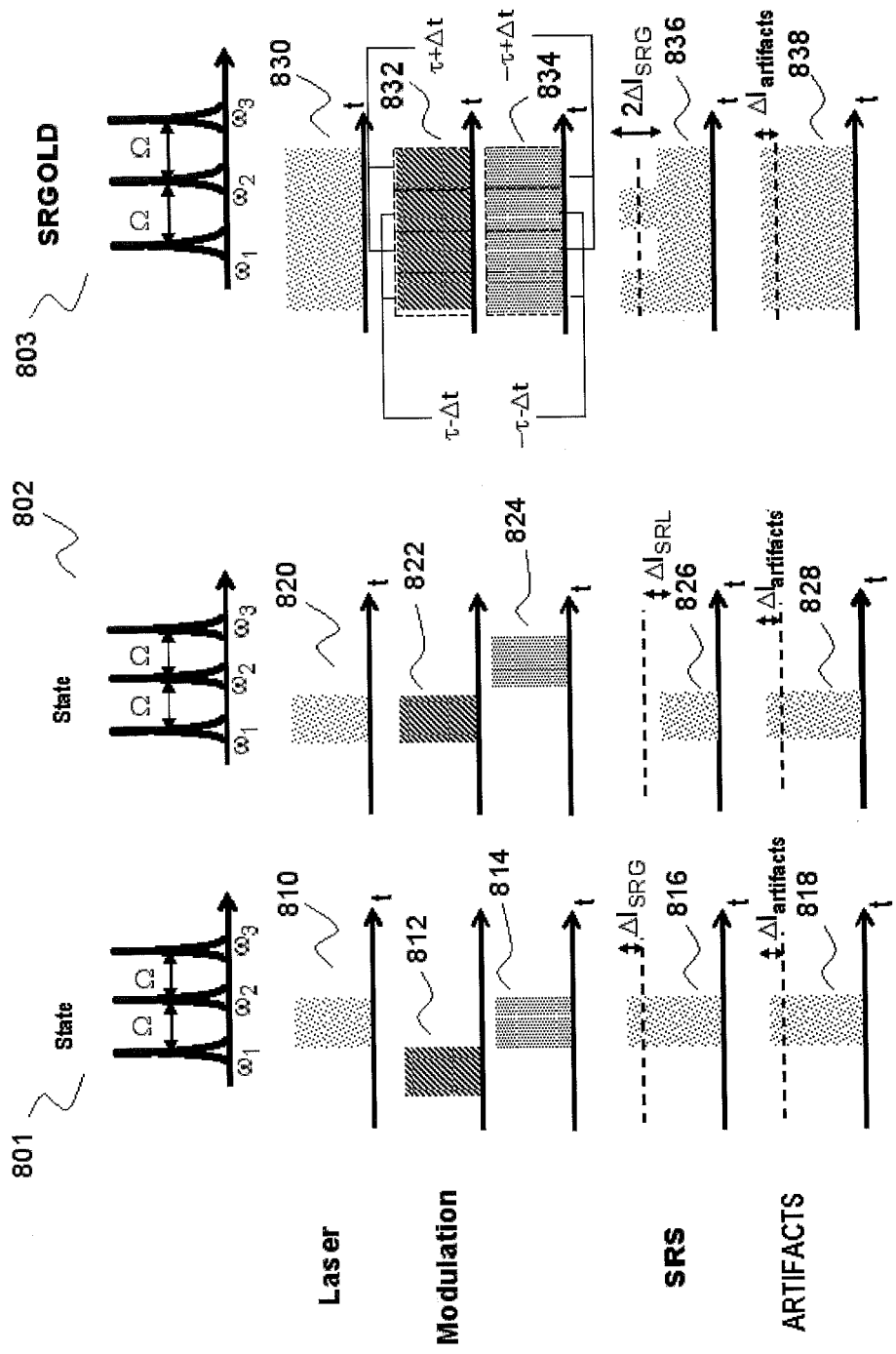
FIG. 15, a table illustrating the signals detected (SRS signals and artifacts) in the example implementation of the device shown in FIG. 13.

Thus, FIG. 13 shows an example embodiment of an SRS detection device implementing a time delay modulation. FIGS. 14A to 14C schematically show the interactions in the sample in this example and FIG. 15 shows a table illustrating the signals detected (SRS signals and artifacts) in the example implementation of the device shown in FIG. 13.

In the device in FIG. 13, a delay line 58 is arranged in a channel common to the trains of pulses at the angular frequencies $\omega_1$ and $\omega_3$. Alternatively, the delay line could be located in the channel of the Laser pulses (angular frequency $\omega_2$). This delay line allows a time delay modulated at a modulation frequency $f_1$ to be introduced between the pulses at the angular frequencies $\omega_1$ and $\omega_3$ and the pulses at the angular frequency $\omega_2$, as is explained by means of FIGS. 14A and 14B. The delay line allows a variation to be introduced into the optical path. The variation in the optical path may be obtained mechanically, between two positions. Alternatively, the delay line may comprise an acousto-optic deflector alternating between two angles in order to generate two optical path lengths. By adjusting delay lines specific to each Idler and Signal channel (see for example the delay lines 54, 56 in FIG. 4), a set delay of $2\tau$ is introduced between the pulses at the angular frequencies $\omega_1$ and $\omega_3$. Modulation of the delay line 58 (FIG. 13) allows a time delay varying between $\pm\Delta t$ at the modulation frequency $f_1$ to be introduced such that the pulses at the angular frequencies $\omega_2$ and $\omega_3$ are superposed in the sample for a time period T (State a, FIG. 14A) and the pulses at the frequencies $\omega_1$ and $\omega_2$ (State b, FIG. 14B) are superposed in the following time period T, the states a and b alternating at the modulation frequency $f_1$ (FIG. 14C). Synchronous detection of the Laser pulses at the angular frequency $\omega_2$ then allows the signal characterizing the molecular vibrational resonance of the sample to be determined. In state a (column 801, FIG. 15), the pulses at the angular frequencies $\omega_2$ (curve 810) and $\omega_3$ (curve 814) are temporally superposed, whereas the pulses at the angular frequency $\omega_1$ (curve 812) are temporally shifted; as a result the Laser pulses illustrated in curve 816 are subject to an SRG process. Once more, in this example it is assumed that the artifacts are mainly due to the cross Kerr effect and manifest as a positive signal (curve 818). In state b (column 802, FIG. 15), the pulses at the angular frequencies $\omega_2$ (curve 820) and $\omega_1$ (curve 822) are superposed, whereas the pulses at the angular frequency $\omega_3$ (curve 824) are temporally shifted; as a result the Laser pulses illustrated in curve 826 are subject to an SRL process. Once more, the artifacts manifest as a positive signal (curve 828). As above, adjusting the average optical powers of the pulse trains incident on the sample allows the signals due to the artifacts in the SRG and SRL processes to be made equal, for example by zeroing the SRGOLD signal off resonance as was explained above. Thus, during synchronous detection, at the modulation frequency $f_1$, of the pulses issued from the sample at the angular frequency $\omega_2$ (column 803, FIG. 15) the artifacts cancel out (curve 838) whereas the useful SRS signal is increased (curve 836). In FIG. 15, the curves 830, 832 and 834 schematically illustrate this variant of the SRGOLD process described above. The train of pulses at the angular frequency $\omega_2$ is emitted continuously (curve 830) whereas the trains of pulses at the angular frequencies $\omega_1$ and $\omega_3$ are subjected to a modulated time delay (curves 832, 834). It will be noted that variants of the arrangement of the delay lines are possible. It is possible, as is the case in FIG. 13, to provide a delay line in the channel common to the $\omega_1$ and $\omega_3$ pulses, or to provide a delay line in the channel of the pulses at the angular frequency $\omega_2$. In this case, delay lines specific to each Idler/Signal channel allow the delay $2\tau$ between the pulses at the angular frequencies $\omega_1$ and $\omega_3$ to be adjusted. Alternatively, delay lines may be specifically arranged in each Idler/Signal channel, with, in each of the channels, a temporal delay modulated between $\tau-\Delta t$ and $\tau+\Delta t$ for one channel and $-\tau-\Delta t$ and $-\tau+\Delta t$ for the other channel.

Although the optical detection employed in the examples in FIGS. 11A, 11B and 13 was forward-mode detection, back-mode (epi-mode) or endoscopic-mode optical detection, such as illustrated above by means of FIGS. 7B and 7D, could be used. These devices may also be at least partially fibered.

FIGS. 16 to 20 illustrate in greater detail the implementation of variants of the method according to the present description in the case where the pulses are frequency chirped pulses.

FIGS. 16A and 16B are schematics illustrating an example embodiment of a source of trains of spread spectrum pulses. This source for example comprises an ultrashort pulse OPO source 20, typically generating pulses shorter than 200 fs in length, comprising a master laser 24, for example an Nd:YVO laser, emitting pulses 12 at 1064 nm and an OPO laser 22 receiving, from the master laser, frequency doubled pulses 11, at about 532 nm. The OPO laser emits, by optical parametric oscillation, Idler pulses 14 at the angular frequency $\omega_1$ and Signal pulses 16 at the angular frequency $\omega_3$. In each of the Laser, Signal, Idler channels, a time dispersion line (52, 53, 51, respectively) allows the ultrashort pulse to be spread into a temporally longer pulse, typically shorter than 100 picoseconds in length, for example a few picoseconds in length, the angular frequency of which varies linearly with time about a central angular frequency. Thus, FIG. 16B illustrates the pulses output by the OPO. As is known, the time dispersion line may comprise a dispersive material, and, for example, is a glass bar or a prism or grating compressor.

FIGS. 17A to 17C illustrate the interactions in the sample in an implementation of a method according to the present description based on an amplitude modulation, when the pulses are spread spectrum pulses. In comparison with FIGS. 5A to 5C, each pulse exhibits a linear angular frequency gradient as a function of time. However, the implementation of the SRGOLD method is unchanged. In particular, the pulse trains interact in the sample in alternation at a given modulation frequency. It will be observed that at each point in time, the condition $\omega_2-\omega_1=\omega_3-\omega_2=\Omega_R$, where $\Omega_R$ is a molecular vibrational resonant frequency of the sample, is respected, allowing the method according to the present description to be implemented. In this example, an identical time shift between the pulses at the angular frequencies $\omega_1$ and $\omega_2$, on the one hand, and the pulses at the angular frequencies $\omega_2$ and $\omega_3$, on the other hand, may be introduced such that it is possible to probe the molecular vibrational resonant frequencies, a slight time shift between the pulses being equivalent to a variation in the angular frequency difference between the pulses.

Figure 18B:
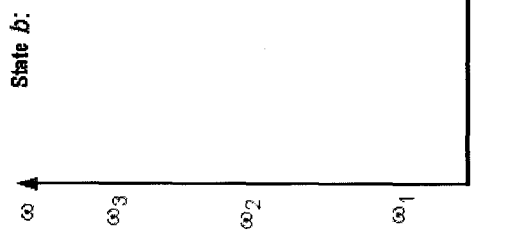
FIGS. 18A to 18C, a schematic illustration of the interactions in the sample, according to a second variant (time delay modulation), with spread spectrum pulses.
Figure 18A:
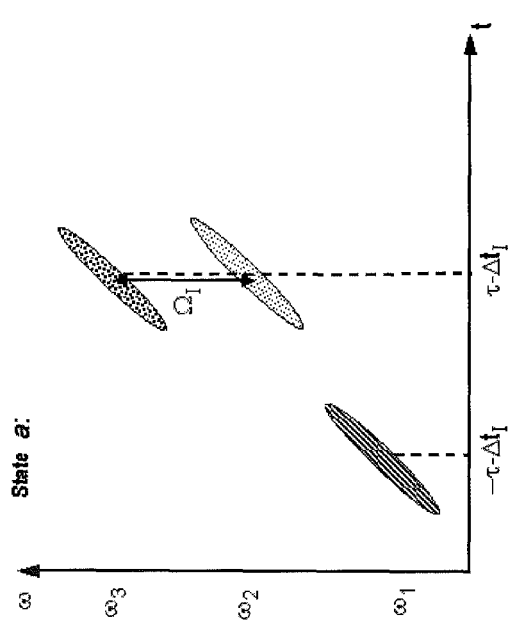
Figure 18C:
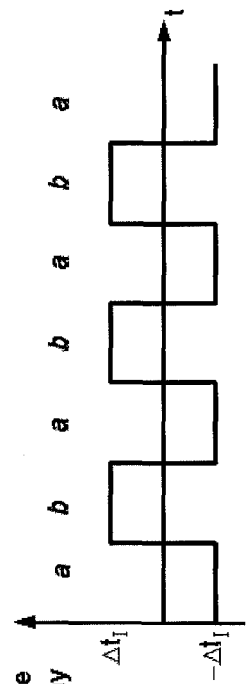
Figure 19A:
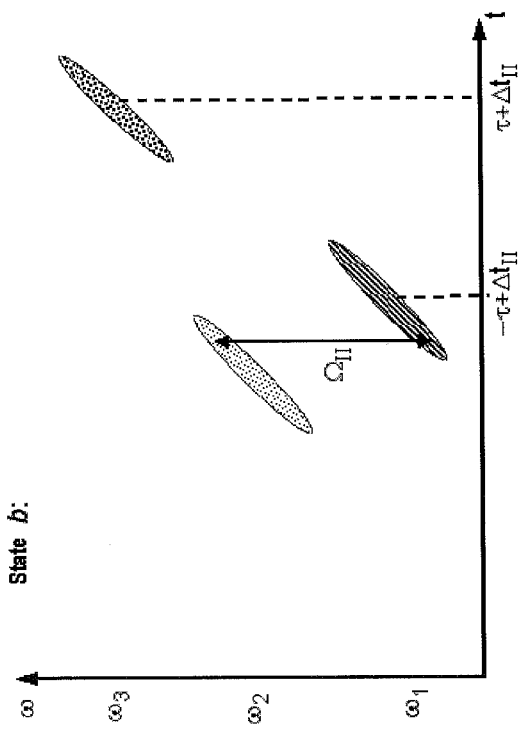
FIGS. 19A to 19C, a schematic illustration of the interactions in the sample, according to a second variant (time delay modulation), with spread spectrum pulses and a variation of the time delay.
Figure 19B:
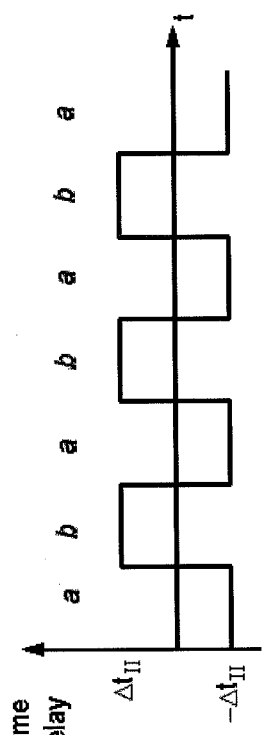
Figure 19C:
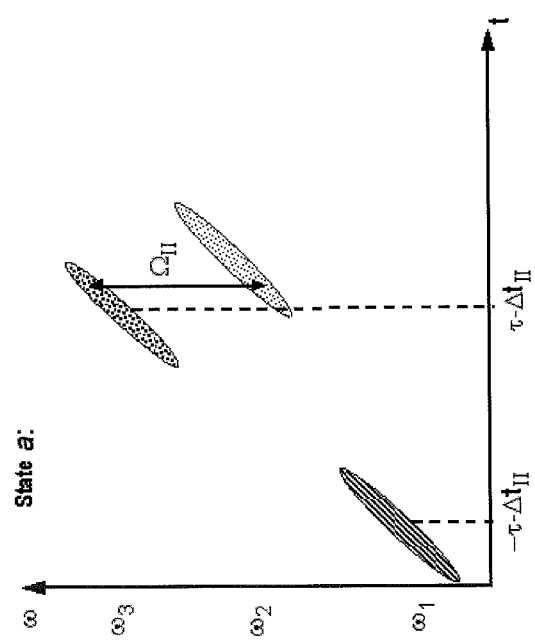

FIGS. 18A to 18C illustrate the interactions in the sample in an implementation of a method according to the present description based on a time delay modulation, when the pulses are spread spectrum pulses. Here again, the method especially described with regard to FIGS. 13 to 15 applies to the frequency chirped pulses. In the case of the use of frequency chirped pulses, it is also possible, by adjusting the time delay, to modify the vibrational resonant frequency of interest, in particular with regard to spectroscopy or hyperspectral imaging applications. In FIGS. 18A and 18B, the time delay is modulated between two values $-\Delta t_1$ and $+\Delta t_1$. This corresponds to a difference $\Omega_1$ between the angular frequencies $\omega_1$ and $\omega_2$, on the one hand, and the angular frequencies $\omega_2$ and $\omega_3$, on the other hand. In FIGS. 19A to 19C, the same pulses are shown but with a modulation of the time delay between two values $-\Delta t_2$ and $+\Delta t_2$, corresponding to a difference $\Omega_2$ between the angular frequencies $\omega_1$ and $\omega_2$, on the one hand, and the angular frequencies $\omega_2$ and $\omega_3$, on the other hand. Thus, varying the time delay allows the spectrum of vibrational resonances to be probed.

Figure 20:
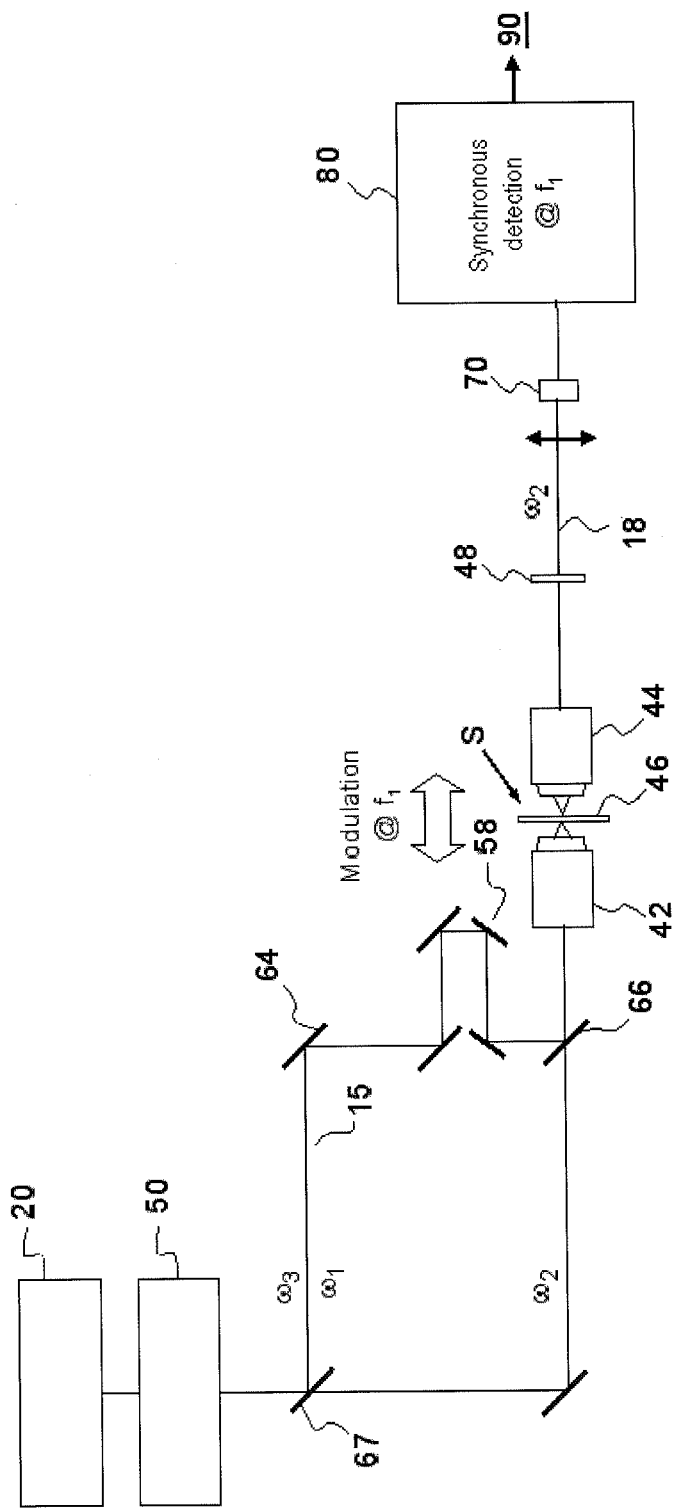
FIG. 20, another embodiment of an SRS detection device according to one variant of the present invention (time delay modulation) and with spread spectrum pulses.

FIG. 20 shows an example embodiment of an SRS detection device according to another example of the present invention, implementing time delay modulation and spread spectrum pulses. In this example, the pulse train emitting source 20 emits ultrashort pulse trains that are time-spread by means of a stretcher 52 in order to form trains of frequency chirped pulses centered on the angular frequency $\omega_2$. The device furthermore comprises a dichroic beam splitter 67 allowing pulses centered on the angular frequency $\omega_2$, on the one hand, and pulses centered on the angular frequencies $\omega_1$ and $\omega_3$ respectively, on the other hand, to be separated. Time delay modulation between the trains of pulses at the angular frequency $\omega_2$ and the trains of pulses at the angular frequencies $\omega_1$ and $\omega_3$ is then possible, for example by means of a delay line 58, as described with reference to FIG. 13 for example. The same synchronous detection method may be implemented for detection of the SRS signal.

FIGS. 21A to 21C illustrate the interactions in the sample in the example of FIG. 20. As illustrated in FIGS. 18A to 18C, modulation takes place between a state a and a state b corresponding to a time delay of $\pm\Delta t$ between the pulses at the angular frequency $\omega_2$ and the pulses at the angular frequencies $\omega_1$ and $\omega_3$. Once more, in this example it is observed that varying the time delay $\Delta t$ allows the angular frequency of the vibrational resonance $\Omega$ of interest to be modified with exceptional ease.

Although described by way of a number of detailed example embodiments, the detection device and method according to the invention comprise various variants, modifications and improvements that will be obvious to those skilled in the art, it being understood that these various variants, modifications and improvements fall within the scope of the invention such as defined by the following claims.

The invention claimed is:

1. A device for detecting a resonant non-linear optical signal of Stimulated Raman Scattering (SRS) type induced in a sample, the device comprising:
   electro-optical means for making interact in the sample, at a first modulation frequency, trains of light pulses of angular frequencies $\omega_1$ and $\omega_2$ and, at a second modulation frequency, trains of light pulses of angular frequencies $\omega_2$ and $\omega_3$, such that $\omega_2-\omega_1=\omega_3-\omega_2=\Omega_R$ where $\Omega_R$ is a molecular vibrational resonant angular frequency of the sample;
   means for synchronous detection at the first and second modulation frequencies of non-linear optical signals resulting from the interaction of the light pulses in the sample; and
   electronic processing means making it possible to obtain, from electronic signals resulting from the synchronous detection, a signal characterizing the molecular vibrational resonance of the sample.

2. The device according to claim 1, in which the electro-optical means comprise an optical source for emitting trains of pulses at the angular frequencies $\omega_1$, $\omega_2$ and $\omega_3$, and means for amplitude modulating the trains of pulses at the angular frequencies $\omega_1$ and $\omega_3$ at the first and second modulation frequencies, respectively.

3. The device according to claim 2, in which the electro-optical means comprise means for amplitude modulating the trains of pulses at the angular frequencies $\omega_1$ and $\omega_3$ at the same modulation frequency but in phase opposition.

4. The device according to claim 2, in which the electro-optical means comprise means for amplitude modulating the trains of pulses at the angular frequencies $\omega_1$ and $\omega_3$ at two separate modulation frequencies that are not multiples of each other.

5. The device according to claim 1, in which the first and second modulation frequencies are identical, and the electro-optical means comprise an optical source for emitting trains of pulses at the angular frequencies $\omega_1$, $\omega_2$ and $\omega_3$, and means for amplitude modulating the train of pulses at the angular frequency $\omega_2$ at the modulation frequency.

6. The device according to claim 1, in which the first and second modulation frequencies are identical, and the electro-optical means comprise an optical source for emitting trains of pulses at the angular frequencies $\omega_1$, $\omega_2$ and $\omega_3$, and at least one delay line making it possible to generate between the trains of pulses at the angular frequencies $\omega_1$ and $\omega_3$ and the trains of pulses at the angular frequency $\omega_2$, a time delay modulated at the modulation frequency.

7. The device accordingly to claim 1, in which the electro-optical means comprise an optical source for emitting trains of frequency chirped pulses centered on the angular frequencies $\omega_1$, $\omega_2$ and $\omega_3$, respectively.

8. The device according to claim 7, in which the emitting optical source furthermore comprises a delay line allowing an identical time shift to be generated between the pulses at the angular frequencies $\omega_1$ and $\omega_2$, on the one hand, and the pulses at the angular frequencies $\omega_2$ and $\omega_3$, on the other hand, in such a way as to make the molecular vibrational resonant frequency of the sample at which the non-linear optical signal is detected vary.

9. The device according to claim 7 in that it depends on claim 6, in which the emitting optical source comprises a generator of trains of frequency chirped pulses centered on the angular frequency $\omega_2$ and a dichroic beam splitter making it possible to separate pulses centered on the angular frequency $\omega_2$, on the one hand, and pulses centered on the angular frequencies $\omega_1$ and $\omega_3$, respectively, on the other hand.

10. The device according to claim 1, is at least partially fibered.

11. A method for detecting a resonant non-linear optical signal of Stimulated Raman Scattering (SRS) type induced in a sample, comprising:
   interacting in the sample, at a first modulation frequency, trains of light pulses of angular frequencies $\omega_1$ and $\omega_2$ and, at a second modulation frequency, trains of light pulses of angular frequencies $\omega_2$ and $\omega_3$, such that $\omega_1-\omega_1=\omega_3-\omega_2=\Omega_R$ where $\Omega_R$ is a molecular vibrational resonant angular frequency of the sample;
   synchronous detection at the first and second modulation frequencies of non-linear optical signals resulting from the interaction of the light pulses in the sample; and
   electronic processing making it possible to obtain, from electronic signals resulting from the synchronous detection, a signal characterizing the molecular vibrational resonance of the sample.

12. The method according to claim 11 comprising the emission of trains of pulses at the angular frequencies $\omega_1$, $\omega_2$ et $\omega_3$ and the amplitude modulation of the trains of pulses at the angular frequencies $\omega_1$ and $\omega_3$ at the first and second modulation frequencies, respectively.

13. The method according to claim 12, in which the trains of pulses at the angular frequencies $\omega_1$ and $\omega_3$ are amplitude modulated at the same modulation frequency but in phase opposition.

14. The method according to claim 12, in which the trains of pulses at the angular frequencies $\omega_1$ and $\omega_3$ are amplitude modulated at two separate modulation frequencies that are not multiples of each other.

15. The method according to claim 11, in which, the first and second modulation frequencies being identical, it comprises emitting trains of pulses at the angular frequencies $\omega_1$, $\omega_2$ and $\omega_3$, and amplitude modulating the trains of pulses at the angular frequency $\omega_2$ at the modulation frequency.

16. The method according to claim 11, in which, the first and second modulation frequencies being identical, it comprises emitting trains of pulses at the angular frequencies $\omega_1$, $\omega_2$ and $\omega_3$, and generating between the trains of pulses at the angular frequencies $\omega_1$ and $\omega_3$ and the trains of pulses at the angular frequency $\omega_2$, a time delay modulated at the modulation frequency.

17. The method according to claim 11, in which the pulses are frequency chirped pulses centered on the angular frequencies $\omega_1$, $\omega_2$ and $\omega_3$, respectively.

18. The method according to claim 17, furthermore comprising generating an identical time shift between the pulses at the angular frequencies $\omega_1$ and $\omega_2$, on the one hand, and the pulses at the angular frequencies $\omega_2$ and $\omega_3$, on the other hand, in such a way as to detect a non-linear optical signal characterizing another molecular vibrational resonant frequency of the sample.

19. The method according to claim 16, in which the pulses are frequency chirped pulses centered on the angular frequencies $\omega_1$, $\omega_2$ and $\omega_3$, respectively.

20. The method according to claim 19, comprising generating trains of frequency chirped pulses centered on the angular frequency $\omega_2$, and separating the pulses into pulses centered on the angular frequency $\omega_2$, on the one hand, and pulses centered on the angular frequencies $\omega_1$ and $\omega_3$, respectively, on the other hand.

* * * * *